(12) United States Patent
Shattuck

(10) Patent No.: US 12,100,311 B1
(45) Date of Patent: Sep. 24, 2024

(54) METHOD AND SYSTEM FOR PROVIDING KINESTHETIC AWARENESS

(71) Applicant: PantherTec Inc., Evergreen, CO (US)

(72) Inventor: Jo Shattuck, Evergreen, CO (US)

(73) Assignee: PantherTec Inc., Evergreen, CO (US)

( * ) Notice: Subject to any disclaimer, the term of this patent is extended or adjusted under 35 U.S.C. 154(b) by 468 days.

(21) Appl. No.: 17/200,658

(22) Filed: Mar. 12, 2021

Related U.S. Application Data

(63) Continuation-in-part of application No. 17/133,342, filed on Dec. 23, 2020, now Pat. No. 11,482,130, which is a continuation of application No. 16/044,506, filed on Jul. 24, 2018, now Pat. No. 10,909,878.

(60) Provisional application No. 62/536,303, filed on Jul. 24, 2017.

(51) Int. Cl.
  *G09B 19/00* (2006.01)
  *A63B 24/00* (2006.01)
  *G09B 5/06* (2006.01)

(52) U.S. Cl.
  CPC ........ *G09B 19/003* (2013.01); *A63B 24/0062* (2013.01); *G09B 5/06* (2013.01); *A63B 2220/40* (2013.01); *A63B 2220/802* (2013.01); *A63B 2220/803* (2013.01); *A63B 2220/836* (2013.01)

(58) Field of Classification Search
  CPC .... G09B 19/003; G09B 5/06; A63B 24/0062; A63B 2220/802; A63B 2220/803; A63B 2220/836
  See application file for complete search history.

(56) References Cited

U.S. PATENT DOCUMENTS

| | | | |
|---|---|---|---|
| 2013/0041617 A1* | 2/2013 | Pease | A43B 3/34 702/139 |
| 2013/0053190 A1 | 2/2013 | Mettler | |
| 2014/0095972 A1 | 4/2014 | Molesky et al. | |
| 2014/0143642 A1* | 5/2014 | Cameron | G06F 3/0483 715/201 |

(Continued)

FOREIGN PATENT DOCUMENTS

WO    2011007545 A1    1/2011

OTHER PUBLICATIONS

International Search Report and Written Opinion in International Application No. PCT/US21/64972 dated Mar. 25, 2022, 9 pages.

*Primary Examiner* — Timothy A Musselman
(74) *Attorney, Agent, or Firm* — Suiter Swantz IP

(57) ABSTRACT

A method and system for providing kinesthetic awareness may include, but is not limited to, capturing a set of training data with a plurality of sensors of a kinesthetic awareness tool, analyzing the set of training data based on an impact level of the plurality of sensors and a response range of the plurality of sensors, generating a position response based on the analysis of the set of training data, comparing the position response to a target response, and generating a numerical response based on a comparison of the position response to a target response. The method and system may include, but is not limited to, generating a response signal if the numerical response is within a configurable feedback threshold, and outputting the response signal via the plurality of feedback devices. The method and system may receive or obtain reference data, with which the target response may be determined.

38 Claims, 14 Drawing Sheets

(56) References Cited

U.S. PATENT DOCUMENTS

| | | |
|---|---|---|
| 2014/0260677 A1* | 9/2014 | Dojan ................ A63B 24/0062 73/862.045 |
| 2015/0079565 A1 | 3/2015 | Miller et al. |
| 2016/0049089 A1 | 2/2016 | Witt |
| 2016/0199693 A1 | 7/2016 | Vermilyea et al. |
| 2018/0161623 A1 | 6/2018 | Nejezchleb |
| 2019/0027058 A1 | 1/2019 | Shattuck |
| 2019/0054347 A1 | 2/2019 | Saigh et al. |
| 2021/0046276 A1 | 2/2021 | Papania |

* cited by examiner

METHOD AND SYSTEM FOR PROVIDING KINESTHETIC AWARENESS

CROSS-REFERENCE TO RELATED APPLICATIONS

The present application is related to and claims benefit of the earliest available effective filing date from the following applications: The present application constitutes a continuation-in-part of U.S. patent application Ser. No. 17/133,342, filed Dec. 23, 2020; which is a continuation application of U.S. Pat. No. 10,909,878, issued Feb. 2, 2021; which is a regular (non-provisional) patent application of U.S. Provisional Patent Application No. 62/536,303, filed Jun. 24, 2017; which are each incorporated herein by reference in the entirety.

FIELD OF THE INVENTION

The present disclosure relates generally to wearable physical fitness activity trackers. In particular, the present disclosure relates to a method and system for providing kinesthetic awareness.

BACKGROUND

Current wearable physical fitness activity trackers include, but are not limited to, personal electronic device applications (e.g., smartphone, tablet, phablet, or the like), peripheral devices configured to communicatively couple to the smartphone applications, peripheral devices configured to communicatively couple to computers, standalone peripheral devices, and the like. The wearable physical fitness activity trackers are configured to record select motion data and/or select physiological data for review and analysis. However, the wearable physical fitness activity trackers offer limited types of information such as step count, amount of time sitting, and/or heart rate (HR), resulting in limited data being taken into account when monitoring the wearer. In addition, most of the information is offered post-activity, resulting in a delay between the "doing" of an activity and the "analyzing and reviewing" of the activity. Further, the wearable physical fitness activity trackers have limited capability to record any specificity of select motion data and/or physiological data related to the context of the current task, resulting in a generic response to specific actions by a particular individual. In this regard, it would be beneficial to provide a system and method that addresses the limitations provided above.

SUMMARY

A system for providing kinesthetic awareness is disclosed, in accordance with one or more embodiments of the present disclosure. In one embodiment, the system may include a kinesthetic awareness tool for providing kinesthetic awareness. In another embodiment, the kinesthetic awareness tool may include a controller. In another embodiment, the controller may be communicatively coupled to a plurality of sensors. In another embodiment, the controller may include one or more processors. In another embodiment, the one or more processors may be communicatively coupled to memory. In another embodiment, the one or more processors may be configured to execute a set of program instructions maintained in the memory and configured to cause the one or more processors to capture a set of training data with the plurality of sensors, analyze the set of training data based on an impact level of the plurality of sensors and a response range of the plurality of sensors, generate a position response based on the analysis of the set of training data, compare the position response to a target response, and generate a numerical response based on a comparison of the position response to a target response.

A method for providing kinesthetic awareness is disclosed, in accordance with one or more embodiments of the present disclosure. In one embodiment, the method may include, but is not limited to, capturing a set of training data with a plurality of sensors of a kinesthetic awareness tool. In another embodiment, the method may include, but is not limited to, analyzing the set of training data based on an impact level of the plurality of sensors and a response range of the plurality of sensors. In another embodiment, the method may include, but is not limited to, generating a position response based on the analysis of the set of training data. In another embodiment, the method may include, but is not limited to, comparing the position response to a target response. In another embodiment, the method may include, but is not limited to, generating a numerical response based on a comparison of the position response to a target response.

A kinesthetic awareness tool for providing kinesthetic awareness is disclosed, in accordance with one or more embodiments of the present disclosure. In one embodiment, the kinesthetic awareness tool may include a controller. In another embodiment, the controller may be communicatively coupled to a plurality of sensors. In another embodiment, the controller may include one or more processors. In another embodiment, the one or more processors may be communicatively coupled to memory. In another embodiment, the one or more processors may be configured to execute a set of program instructions maintained in the memory and configured to cause the one or more processors to capture a set of training data with the plurality of sensors, analyze the set of training data based on an impact level of the plurality of sensors and a response range of the plurality of sensors, generate a position response based on the analysis of the set of training data, compare the position response to a target response, and generate a numerical response based on a comparison of the position response to a target response.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION OF THE INVENTION

Figure 1:
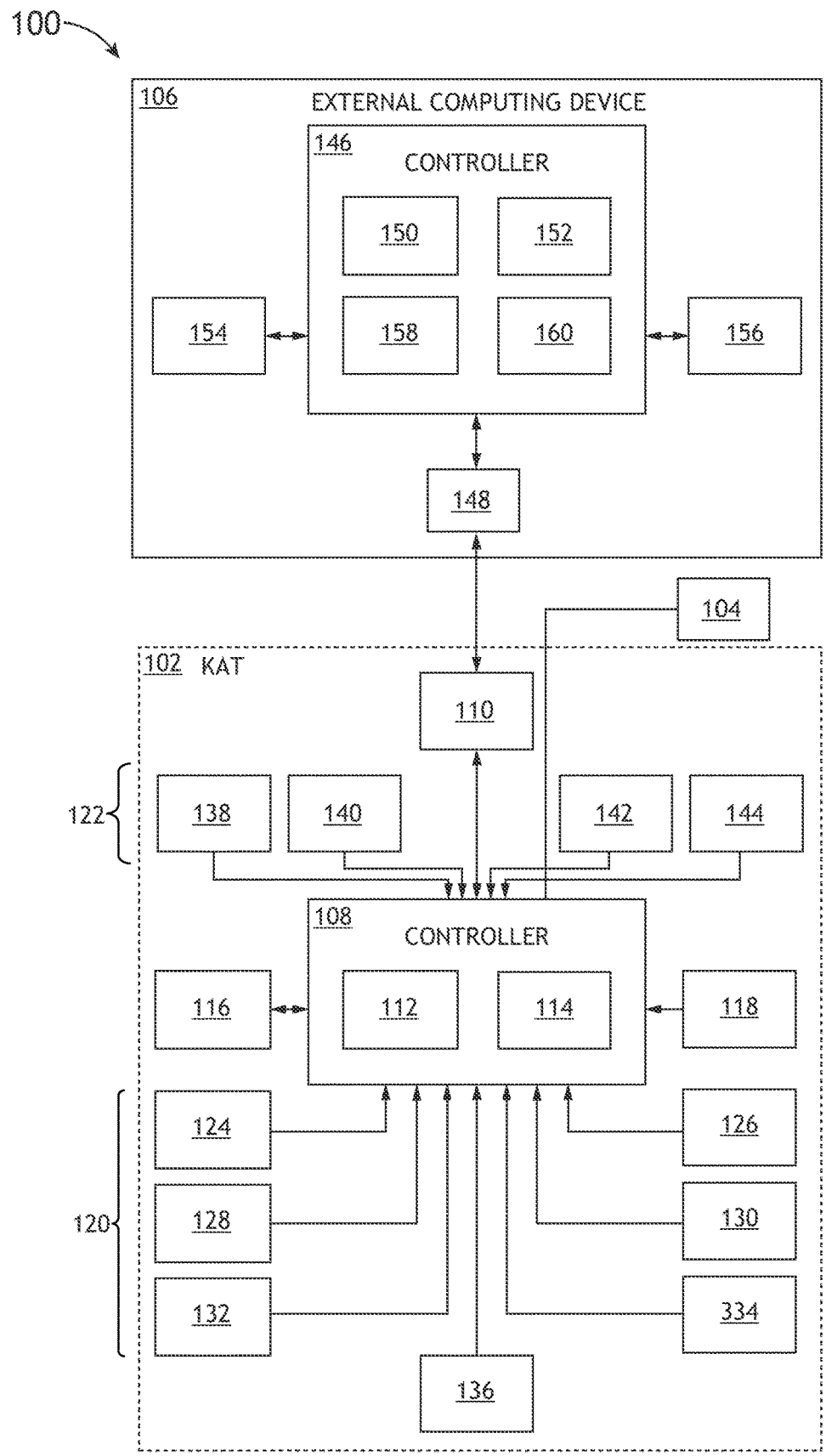
FIG. 1 illustrates a simplified block diagram illustrating a system for providing kinesthetic awareness, in accordance with one or more embodiments of the present disclosure.

All illustrations of the drawings are for the purpose of describing selected versions of the present disclosure and are not intended to limit the scope of the present disclosure.

Current wearable physical fitness activity trackers include, but are not limited to, personal electronic device applications (e.g., smartphone, tablet, phablet, or the like), peripheral devices configured to communicatively couple to the smartphone applications, peripheral devices configured to communicatively couple to computers, standalone peripheral devices, and the like. The wearable physical fitness activity trackers are configured to record select motion data and/or select physiological data for review and analysis. However, the wearable physical fitness activity trackers offer limited types of information such as step count, amount of time sitting, and/or heart rate (HR), resulting in limited data being taken into account when monitoring the wearer. In addition, most of the information is offered post-activity, resulting in a delay between the "doing" of an activity and the "analyzing and reviewing" of the activity. For example, the wearable physical fitness activity trackers lack the ability for subsequent, nearly real-time, or real-time instruction as to what is a correct or incorrect motion and/or a correct or incorrect behavior causing the motion (e.g., a stance or body position). Further, the wearable physical fitness activity trackers have limited capability to record any specificity of select motion data and/or physiological data related to the context of the current task, resulting in a generic response to specific actions by a particular individual. For example, the wearable physical fitness activity trackers lack the ability to identify a type or quality of a motion and/or a behavior causing the motion, including whether the motion and/or the behavior causing the motion is correct or incorrect.

Embodiments of the present disclosure are also directed to a system and method for providing kinesthetic awareness, or the knowledge of one's own body in a particular time and/or space, including in a dynamic state (e.g., during movement) or a static state (e.g., staying still). Embodiments of the present disclosure are also directed to a kinesthetic awareness tool (KAT) to be used for training feedback, which is managed by a controller monitoring one or more sensors capture training and performance data, analyzing that data, and controlling one or more feedback devices.

Embodiments of the present disclosure are directed to motion capture, correction, and feedback tools in human kinetics and kinematics. Embodiments of the present disclosure are also directed to monitoring and recording body or tool movements, monitoring and recording bio-physiological and neuro-physiological data, and providing various forms of feedback to increase a user's kinesthetic awareness based on the monitored and recorded body movements, tool movements, bio-physiological data, and/or neuro-physiological data.

In one embodiment, the KAT is a system of instruments configured to combine sensing, monitoring, and recording of inertial measurement units (of distances, positions, angles, velocity) and of bio physiological and neurophysiological data (for example, including but not limited to heart rate, brain waves, muscle activity) from several wearable/handheld devices. In another embodiment, the KAT is configured to provide various delivery methods of feedback (e.g., audio, visual, texture, tactile, haptic, or the like) in multiple methods (e.g., dose, duration, frequency, intensity, type, or the like) in response to the values (e.g., aggregated values or individual values) of those measurements. For example, the feedback may be provided concurrently or nearly-concurrently during real-time movement, intermittently (e.g., at various fixed or random intervals) during real-time movement, or after the real-time movement (e.g., in post-movement review). For instance, the feedback may be individually-customized (e.g., pre-determined by a wearer or by a user to teach proper position for a known particular task, movement, or skill).

It is noted herein "task", "movement", and "skill" are used interchangeably to identify any desired action, pose, and/or exercise, for purposes of the present disclosure.

It is noted herein "position" may refer to any kinematic motion and/or bio-physiological state, for purposes of the present disclosure. For example, "position data" may include information related to, but not limited to, eye movement or tracking; muscle activation, electrocardiogram (ECG or EKG), electromyography (EMG), electroencephalogram (EEG), and/or other muscle or brainwave activity; forces generated from external force plates or third-party force plates with which a wearer may interact; and other physiological information in addition to kinematics or motion data. For instance, the force plates may be positioned external from the wearer, and may be devices the wearer may interact with by approaching and stepping on. In addition, the force plates may be integrated or embedded within an article of clothing (e.g., shoe) worn by the wearer. In general, the force plates may generate position data for/from which feedback may be generated, where the position data may represent amount of force produced on the force plates, symmetries or asymmetries in the production or application of force, mapping one leg or arm versus another leg or arm, or the like during force production, muscle activation, or the like.

It is noted herein a "user" is a person (e.g., a coach, clinician, physical therapist, advisor, consultant, friend, or the like) controlling a session, for purposes of the present disclosure. For example, the user may choreograph the desired motions, exercise, practice movements, or the like to be executed by a wearer (e.g., during individualized practice) or multiple wearers (e.g., members of a team of at least two people during practice of choreographed movements or other types of dependent movements) and determine the overall objective of the exercise. By way of another example, the user may passively move a wearer into or out of positions (e.g., by moving the body of the wearer for the wearer, in instances where the user wants to deliberately position the body and/or in instances where the wearer cannot move their own body (e.g., during neuromotor rehabilitation).

It is noted herein a "wearer" is a person or an animal (e.g., horse, dog, or other animal) wearing or holding the one or more KAT, who is being measured and to whom feedback is provided, for purposes of the present disclosure. In addition, it is noted herein that while the wearer may receive the one or more feedback responses, the user may also receive the results of these sessions. Further, it is noted herein the user may be a wearer, such that a person may act as both user and wearer simultaneously, such that the wearer may set their own parameters.

Embodiments of the present disclosure are also directed to a system that includes one or more wearable devices that record and monitor the positions and movements of said devices while being used in human or animal movement training. In one embodiment, the system has applications in motor skill acquisition, physical therapy, fitness, rehabilitation and motor learning for sports skills and/or the arts. In another embodiment, the present disclosure is a platform of devices containing multiple sensors which capture and record the movements and positions of a body part or object of a user. In another embodiment, the present disclosure is a platform of devices that provides visual, audio, tactile, haptic feedback, or the like to the user regarding their movements, positions, angles, and/or bio-physiological measures of their body (e.g., ECG or EKG, EMG, EEG, and/or other muscle or brainwave activity), and/or the movements/position/angles of the tool or object currently in use. For example, target parameters may be determined by the user or coach, where the target parameters may represent a desired movement or position for a wearer to learn. By way of another example, the feedback provided to the user and/or the wearer during practice may be based on factors including, but not limited to, an algorithm that analyzes an actual internal measurement unit (IMU) data as comparted to a desired IMU, biological and neurological input signals of the multiple sensors, skill level of the user, component of practice, previous practice, and/or user's sleep quality and duration.

In another embodiment, the operation algorithms for the KAT are based on a number of scientific principles known to be important factors in improve human movement performance. For example, the scientific principles include, but are not limited to, accurate proprioception, degrees of freedom, variable feedback, practice schedules (e.g., ranging between blocked-practice schedules, random-blocked practice schedules, and random practice schedules), movement variability and motor control strategies, each being described in the context of the dynamical systems theory of motor learning as follows:

Proprioception: The knowledge of one's body in time and space. In human movement, proper proprioception (knowledge of one's body in time and space) is essential to motor learning.

Degrees of Freedom: There are multiple ways the body, (e.g., with its various muscles and joints), performs a movement. In motor learning and human biomechanics, this is known as the degrees-of-freedom movement problem. This problem is partially resolved in the class of the dynamical systems theories.

Dynamical Systems Perspective: The dynamical systems perspective (DSP) suggests that all human movement involves dynamic self-organization of multiple body systems (e.g., the proprioception, vestibular, visual motor, neuromuscular system, and/or the like), working together to solve a degrees-of-freedom movement problem. The attempts to solve the degrees-of-freedom movement problem contain inherently varying patterns, even when the individual actively intends to repeat the same movement. These inherently varying patterns (e.g., as known as movement variability) are believed to play an important role in adaptability, flexibility and subsequent increased performance under stressful conditions, as opposed to being detrimental to optimal performance.

Motor control strategies: Small muscular adjustments (conscious or unconscious) that occur during a movement are thought to counter this inherent movement variability. Improving motor control within a small range of movement variability systems appears to create the "best" movements (e.g., movements with a desired level or flexibility and/or adaptability during performance).

Feedback: While any body movement includes feedback through the body's somatosensory afferent pathways (e.g., pathways that allows you to feel the weight of an object or know where how your hand is positioned), additional information may be provided to the performer. For example, motor learning principles of feedback during practice may involve internal feedback (e.g., on a body part), external feedback (e.g., on an object outside the body such as, but not limited to, a wall, floor, net, or the like), augmented feedback (e.g., in addition to natural somatic sensations), descriptive feedback (e.g., what was done) and/or prescriptive feedback (e.g., what 'should' be done). It is noted herein the type and timing of the delivery of the feedback (e.g., frequency, duration, intensity, of the feedback) and/or content of the feedback (e.g., qualitative or quantitative) may affect the effectiveness of practice. For example, a vibratory pattern having a sub-threshold stochastic resonance may improve speed of a hopping task. These principles may apply to both continuous skills (e.g., including, but not limited to, walking, running, or the like) discreet skills (e.g., including throwing, sitting, standing, or the like), and to either open skills and/or closed skills. For example, open skills may be dependent on the environment and task constraints, while closed skills may be pre-determined and not dependent on the environment and task constraints).

In this regard, additional information may be provided to the performer with the KAT system in addition to feedback through the somatosensory afferent pathways. For example, one novel method of delivering this additional information is Kinetic Feedback method. For instance, this feature produces pulses, or small internal movements in 3 possible axes, and multiple speeds (e.g., felt as gentle "pulls or pushes" in specific directions) to guide the user with prescriptive concurrent feedback as the movement is being executed.

Practice: There are several pedagogical approaches to practice. On one end of the spectrum of skill break-down is the 'progression of skills', where the whole movement is separated into smaller components and each component slowly added to the whole movement as each skill is mastered. On the other end is 'entirety', where the whole movement is practiced in a single attempt. A particular type of practice schedule may be chosen to increase the efficiency, adaptability, and longevity of motor skills. For example, a "blocked practice" schedule can consist of extended blocks of time (e.g., practicing Task A for 15 minutes, Task B for 15 minutes, and Task C for 15 minutes in a single block of time, or the like). These longer blocks of time allow for a deeper encoding for the motor memory of a novel skill, sometimes called the cognitive or fast stages of motor skill acquisition, and is suitable for learners in the very early stages. By way of another example, a "random-blocked practice" schedule may consist of short blocks of time (e.g., practicing Task A for 5 minutes, Task B for 5 minutes, and Task C for 5 minutes in a single block of time, or the like). The random-blocked practice schedule may be suitable for learners in the middle, associative, or slow stages of motor skill acquisition. By way of another example, a "random practice" schedule consists of quickly switching from task to task in even shorter blocks of time such as a matter of seconds (e.g., practicing Task A for 20 seconds, Task B for 30 seconds, back to Task A for 10 seconds, Task C for 20 seconds in a single block of time, or the like). The random practice schedule may be suitable for experienced learners in the later, automaticity stage of motor skill acquisition, and may encourage skill adaptability and transferability. The effectiveness of these practice types has been shown to be based in part on factors including, but not limited to, skill, context and/or task dependency.

Sleep: Long Term Potentiation (LTP) or slow-learning is a type of neural re-organization involving the growth of new receptors in postsynaptic cells in the C1 and C3 regions of the hippocampus. Greater sleep quality and duration has been shown to have a linear correlation with increased LTP (learning and retention of skills). The KAT's algorithms account for the sleep factor in addition to the past performance history in each practice using a sleep history input option in a user interface, as described in detail further herein.

In another embodiment, the KAT operates under principles of human biomechanics and neuroscience, taking advantage of the elements known to promote successful acquisition, re-acquisition, retention and transfer of both fine (small muscle) and gross (large muscle) movements. The KAT implements these principles based on empirical research into the algorithms used to interpret the sensor inputs, analyze the movements, account for movement variability, and create feedback and practice schedules suited for the skill of the user and temporal variations in motor learning stage, with the end goal of motor skills long term retention and accuracy in improvement of motor skills.

In some embodiments, the system and method for providing kinesthetic awareness may be used for short-term improvements to correct or improve specific movement and/or positions as the user is practicing; the present disclosure can also be used for long-term use in applications (e.g., when a movement is retarded by movement disorder, disease or other physical limitations). For example, the present disclosure may assist a user to recalibrate the proprioceptors and/or mechanoreceptors (e.g., which are units of cells in the body that send information back to the brain about the position, movement, and/or muscle tension of the limbs and joints in time and space).

In some embodiments, the system and method for providing kinesthetic awareness may be used to help patients perform these post-surgery exercises correctly. It is noted herein using correct movements and achieving the range of motion is critical for optimal recovery in physical therapy exercises. The pre-surgery range of motion is usually re-achieved by gradually increasing the target range of motion (ROM) as the tissue heals, during post-surgery exercises. After knee surgery, walking squats are a common exercise. When attached to the knee, the KAT may be set to a specific distance that reflects the desired degree of angle of the knee, by aiming the sensor at the floor or other part of the body. It is noted herein embodiments of the present disclosure include instructions about providing feedback to the patient to let them know if his leg angle is within the desired range.

In some embodiments, the system and method for providing kinesthetic awareness may be used for monitoring physiological movements and providing feedback to increase a user's kinesthetic awareness. In some embodiments, the system and method for providing kinesthetic awareness may be used to improve proprioception/motor control by creating new neural pathways. In some embodiments, the system and method for providing kinesthetic awareness includes using the KAT to combine sensing and recording of positional and bio-physiological measurements and provide various types of feedback in response to the values of those measurements.

FIGS. 1-6 in general illustrate a system 100 for providing kinesthetic awareness, in accordance with one or more embodiments of the present disclosure.

In one embodiment, the system 100 includes one or more kinesthetic awareness tools 102 (KAT 102). It is noted herein "KAT 102" may represent a single KAT 102 or multiple KAT 102, as described throughout the present disclosure.

In another embodiment, the system 100 includes one or more external monitoring devices 104. In another embodiment, the system 100 includes one or more external computing devices 106.

In another embodiment, the KAT 102 is a wearable device that measures, records, and monitors a wearer's positions and movements. For example, the KAT 102 may be a wearable device that is attached to the wearer. By way of another example, the KAT 102 may be a holdable device. By way of another example, the KAT 102 may be attached to a tool or object that is used or held by the wearer. It is noted herein the placement of the KAT 102 ensures that the movement made by the user is the desired movement, in the desired direction, within the desired range of motion, and/or the pose held is the desired pose.

It is noted herein one or multiple KAT 102 may be attached to or held onto by a single wearer. For example, where there are multiple KAT 102, the multiple KAT 102 may work together to measure, record, and monitor the wearer's positions and movements. In addition, it is noted herein one or multiple KAT 102 may be attached to or held onto by multiple wearers. For example, where there are multiple wearers, with each wearer being in possession of one or multiple KAT 102, the one or multiple KAT 102 in possession of the multiple wearers may work together to measure, record, and monitor the multiple wearers' positions and movements, as well as choreograph and/or synchronize the multiple wearers' positions and movements.

In another embodiment, the KAT 102 includes a controller 108. The controller 108 may be communicatively coupled with any of the components of the system 100 including, but not limited to, the one or more external monitoring devices 104, the one or more external computing devices 106, or the like via one or more communication interfaces 110. For example, the one or more communication interfaces 110 may include a wireline (e.g., copper wire, fiber optic cable, wired port, or the like) or wireless connection (e.g., RF coupling, IR coupling, data network wireless communication (e.g., Wi-Fi, WiMAX, Bluetooth, 3G, 4G, 4G LTE, 5G, or the like), near-field communication (NFC), or the like).

The controller 108 may include one or more processors 112 configured to execute program instructions maintained on memory 114 (e.g., a memory medium, memory device, or the like). The controller 108 may be programmed to allow for software and/or firmware upgrades or changes to the KAT 102. The one or more processors 112 of the controller 108 may execute any of the various process steps described throughout the present disclosure. For example, the one or more processors 112 of the controller 108 may be configured to perform one or more of capturing a set of reference data with one or more sensors, receiving an impact level and a response range of the one or more sensors, analyzing the set of reference data based on the impact level and the response range of the one or more sensors, generating a target response based on the analysis of the set of reference data, capturing a set of training data with the one or more sensors, analyzing the set of training data based on the impact level and the response range of the one or more sensors, generating a position response based on the analysis of the set of training data, comparing the position response to the target response, generating a response value based on the comparison of the position response to the target response, generating a response signal if the response value is within a configurable feedback threshold, providing the response signal to one or more feedback devices, receiving one or more additional inputs from one or more external monitoring devices, combining the one or more additional inputs and the set of reference data, receiving the impact level and the response range for the one or more sensors from one or more external computing devices, transmitting the impact level and the response range for the one or more sensors to one or more external computing devices, storing the impact level and the response range for the one or more sensors with a personal identifier, receiving one or more additional inputs from one or more external monitoring devices, combining the one or more additional inputs and the set of training data, and/or transmitting the set of training data to one or more external computer devices. It is noted herein the controller 108 may be configured with one or more feed forward or feedback control loops for modification of the various process steps described throughout the present disclosure.

In another embodiment, a user interface 116 is communicatively coupled to or integrated with the controller 108. For example, the user interface 116 may include a display used to display data of the system 100 to a wearer. In another embodiment, one or more user input devices 118 are communicatively coupled to or integrated with the controller 108.

In one embodiment, the KAT 102 includes one or more sensors 120 and one or more feedback devices 122. In general, the KAT 102 may include 1, 2, . . . up to an N number of sensors 120 and/or 1, 2, . . . up to an N number of feedback devices 122. The KAT 102 provides feedback to the user regarding the user's movements/position, and/or the movement/position of the KAT 102 in three axes (e.g., up/down, front/back, side/side). By way of another example, the wearer sees, feels and/or hears the feedback indicating the wearer's error (e.g., range too big, range too small, or the like), allowing the wearer to make adjustments. Any or all of the one or more sensors 120 and/or the one or more feedback devices 122 may be communicatively coupled to the controller 108.

In another embodiment, targets may be set (captured) by the one or more sensors 120 and adjusted via feedback from the one or more feedback devices 122. The targets may be captured with "Easy mode", where data is captured during live real-time movement, captured manually through the KAT 102, and/or manually input through the KAT 102 and/or an associated software application. The capturing may be initiated by pressing a triggering key (e.g., a user input device 118 including a physical button, an on-screen graphical user interface (GUI) button, or the like) on the KAT 102 and/or the external computing device 106. For example, the triggering key may be pressed once to initiate a capture window to perform a real-time capture, during which the movement is performed. For instance, where the triggering key is pressed once to activate the capture window, the capture window may remain activated until deactivated by pressing the triggering key. In addition, where the triggering key is pressed once to initiate the capture window, the capture window may remain activated only for a period of time, which may be pre-programmed or may be set by the user or wearer via a software application. By way of another example, the triggering key may be pressed and held during the entire timeframe in which the movement is performed. In this regard, the timeframe for a motion is bounded by either one pressing of the triggering key (e.g., where the timeframe is programmed), two pressings of the triggering key (e.g., where the timeframe is defined by the input of the pressings of the triggering key), or by a pressing and holding of the triggering key (e.g., where the timeframe is defined by the continuous input of the triggering key).

The controller 108 may allow for the simultaneous collection of data from the one or more sensors 120. For example, the sampling rate of each of the one or more sensors 120 may be adjusted independently by the controller 108. In another embodiment, data collected by the one or more external monitoring devices 106 may be transmitted to the controller 108, which may then be combined with the data from the one or more sensors 120. In another embodiment, upon processing data acquired from the one or more sensors 120, and optionally data from the external monitoring device 106, the controller 108 may enable one or more of the one or more feedback devices 122 to produce a signal that is perceptible to the wearer.

It is noted herein the one or more sensors 120 and/or the one or more external monitoring devices 104 may be considered a fixed sampling rate sensor or a variable sampling rate sensor. For example, the fixed sampling rate sensor may be configured to provide samples at 1 Hz to 2000 Hz (depending on the maximum sensor ability). By way of another example, the variable sampling rate sensors provide data whenever data is available. The presence of multiple sensors with different sampling rates may require a sample alignment mechanism. For example, the controller 108 may align the data according to the highest-frequency sensor. In this non-limiting example, if only a sensor with a 100 Hz sampling rate and a sensor with a 10 Hz sampling rate are used, the data will be represented using the 100 Hz sampling rate. For the alignment mechanism, two alignment interpolation strategies are available. For example, in a "hold" mode, the slower sample is copied until the new sample arrives. By way of another example, in a linear interpolation mode the "missing" intermediate samples of the slower sensor are interpolated linearly.

The one or more sensors 120 may be configured to measure the position of the KAT 102 in three-dimensional space, and in turn sense if the correct body positions/movements/muscle activations are being achieved. It is noted herein a position or movement is not an arbitrary point in space, but is the aggregation of distances, direction vectors, angles, acceleration, velocity, sequence of events, and time when considered in the kinesthetic sense. As such, the position or movement may be defined by the combined data from the one or more sensors 120.

Data from the one or more sensors 120 may be fed to the controller 108, and the controller 108 may generate a feedback response corresponding to the obtained data. For example, to create the feedback response, the data may be weighted according to parameters input by the user (e.g., allowing the feedback response to be unique to that wearer and/or training session). By way of another example, the feedback response is then compared to adjustable thresholds to determine whether or not a feedback signal is required. If the feedback response falls within a defined feedback range, then the feedback signal is sent, and one or more of the one or more feedback devices 122 produces a signal that is perceptible to the wearer.

The dimension parameters of each of the one or more sensors 120 may be individually adjusted, which may allow for the captures by the one or more sensors 120 to be weighted with more or less 'importance' in the algorithm used to analyze the position or movement of the wearer.

It is noted herein that up-weighting (e.g., applying more importance) and/or down-weighting (e.g., applying less importance) may be referred to as a margin of error (MoE) in a determination of whether a feedback signal should be provided to the wearer. In one embodiment, the Margin of error may be adjustable. For example, the margin of error may be adjusted via one or more user input devices 118 of the KAT 102. In another embodiment, the margin of error may be adjusted via one or more user input devices 156 of a controller 146 of the one or more external computing devices 106, as described in detail further herein. For example, the margin of error may extend on each side of the data, meaning greater than or lower than the target values in a set of reference data.

In another embodiment, the margin of error may be adjusted in a global sense by using a global slider or similarly-operating user input. Being a global option, the operation automatically applies to all of the one or more sensors 120, dimensions, and other parameters including in the target. For example, the global slider may apply a multiplier of standard deviation to all of the one or more sensors 120, dimensions, and other parameters including in the target. By way of another example, the global slider may equally apply to all of the one or more sensors 120, dimensions, and other parameters including in the target.

In another embodiment, the margin of error may be adjusted in a focused sense by applying it to one or more specific dimensions or parameters of the target. For example, the Margin of Error can be adjusted asymmetrically for any Target value when adjusting in a focused sense. It is noted herein the asymmetric adjustment may effectively up-weight and/or down-weight any individual plane. It is noted herein a weighting feature may be beneficial in rehabilitation settings.

For example, the speed of the movement of the KAT 102 may be set to have little or less importance (e.g., is weighted lower) where speed of the movement is not a concern. For instance, the speed of the movement of the KAT 102 may be set to have little or less importance when teaching and/or monitoring a reach and grasp task.

By way of another example, a height setting (e.g., vertical distance jump) could be set for more importance (e.g., is weighted higher). For example, the height setting (e.g., vertical distance jump) could be set for more importance when teaching and/or monitoring a range-of-motion (ROM) task.

By way of another example, suppose a target for a knee angle is 45 degrees. It may be allowable if a wearer bends their knee slightly higher than 45 degrees (e.g., up to 50 degrees), but the wearer should not bend their knee below a certain value (e.g., 44 degrees). An asymmetrical margin (+5/−1) could be set to allow for this customization. The feedback is then based on the Target's mean values and the upper and lower margins—each of which can be individually adjusted in real time during a movement.

In another embodiment, the margin of error may be adjusted in a more programmatic sense by applying system wide adjustments calculated by an artificial intelligence component of the system 100. For example, the artificial intelligence component may analyze the body of reference data and training data for a particular individual, and compare that data to the pre-assembled aggregate multi-person database. For instance, the artificial intelligence component may classify data for multiple people into separate athletic categories, where each category contains people of similar performance data. In addition, the artificial intelligence component may relate the particular individual to one of the predefined athletic classes. Within that class, the artificial intelligence component may find instances of the same movement being attempted by the particular individual. From that information, the artificial intelligence component may project target goals and associated margin of error values derived from the selected athletic category so that the particular individual can be challenged by improved performance goals.

It is noted herein the margin of error may be adjusted depending on the progress of the wearer. For example, the margin of error may be reduced when the ability of the wearer increases, or may be increased when the ability of the wearer decreases.

In another embodiment, the different positions may include multiple associated parameters, with each associated parameter having a separate attribute identifier for quick identification purposes. For example, possible attribute identifiers may include, but are not limited to, various colors, geometric shapes, icons, special-designed icons to indicate various motions, numerical indexing applied as a suffix, or the like. For instance, the possible attribute identifiers may be used by the external computing device 106 when defining parameters to include for feedback or displaying results.

In one non-limiting example, color may be the attribute identifier, as provided in Table 1:

TABLE 1

| Position Zero | X angle | Pink |
|---|---|---|
| Position One | X angle and Y angle | Blue, Blue |
| Position Two | X angle and X acceleration | Maroon, Maroon |
| Position Three | X angle, Z acceleration, electromyography (EMG) muscle activation from auxiliary sensor | Yellow, Yellow, Yellow |

It is noted herein that where there are multiple references for a particular feedback, each/all of the multiple references may need to be achieved for the feedback to be delivered.

In another embodiment, an adjusted margin of error becomes the effective margin of error. In another embodiment, the effective margin of error may help determine how and/or when feedback is provided for each position in the training data. Feedback received by the user or the wearer regarding the training data may be delivered according to the values of the training data relative to the effective margin of error (e.g., the values being the position or movement measured within or outside of the margin of error).

In another embodiment, the feedback may be dependent on a context of how the KAT 102 is being used. For example, the KAT 102 may operate based on one or more context modes (e.g., training modes according to pedagogical frameworks), as described with respect to FIG. 2 in greater detail herein.

In another embodiment, the one or more sensors 120 include one or more central devices for sensing movement in three dimensions. For example, the one or more central devices may include, but are not limited to one or more accelerometers 124, one or more magnetometers 126, one or more gyroscopes 128, or other three-dimensional movement-sensing devices. For instance, the three dimensions x, y, and z are measured by the one or more magnetometers 126 and the one or more gyroscopes 128. In addition, acceleration of the KAT in all three dimensions, x, y, and z are measured by the one or more accelerometers 124.

In another embodiment, the one or more sensors 120 include one or more distortion devices 130 for sensing body movement and positioning. For example, the one or more distortion devices 130 may include, but are not limited to, one or more bend sensors, one or more force transducers, one or more potentiometers, or the like.

In another embodiment, the one or more sensors 120 include one or more reflective devices 132 for sensing body movement and positioning. For example, the one or more reflective devices 132 may include, but are not limited to, sonar systems, Light Detection and Ranging (LiDAR) systems, ultrasonic range finders, or other sound-based or light-based proximity sensors.

In another embodiment, the one or more sensors 120 include one or more proximity devices 134 for sensing body movement and positioning. For example, the one or more proximity devices 134 may include, but are not limited to, infrared sensors, electromagnetic devices, or the like.

In another embodiment, the one or more sensors 120 include one or more eye tracking devices 136 for sensing eye movement and positioning (e.g., sensing, eye motion, duration of eye movement, trajectory-equivalents, or the like). For example, the one or more eye tracking devices 136 may include, but are not limited to, eye focus point devices, eye movement devices, gaze fixation devices, or the like.

In one non-limiting example, the one or more sensors 120 may include the accelerometer 124, the magnetometer 126, the gyroscope 128, and the reflective device 132. The accelerometer 124, the magnetometer 126, the gyroscope 128, and the reflective device 132 may be used to collect nine parameters for calculating the user's position or movement. Three-dimensional orientation of the KAT 102 (e.g., the angle of the x, y, and z axis of the KAT 102) is measured by the magnetometer 126 and the gyroscope 128. Meanwhile, acceleration of the KAT 102 in the x, y, and z directions is measured by the accelerometer 124. The reflective device 132 further measures reference distances along the x, y, and z directions.

It is noted herein it may be desirable to collect additional user or environment data in some situations, such as temperature, humidity, pulse, or the like. As such, in other embodiments, the one or more sensors 120 may further include galvanic skin response sensors, a temperature sensor, a barometer sensor, an angle potentiometer, or neuro-, bio-, or electro-physiology sensors.

It is noted herein the system 100 may include any number or combination of sensors 120, for purposes of the present disclosure.

In one embodiment, the one or more feedback devices 122 include one or more visual devices 138. For example, the one or more visual devices 138 may include, but are not limited to, one or more lights, one or more LEDs, a display screen, special display for use on eyeglasses, traffic light simulation, or other similar devices capable of generating a visual cue. By way of another example, alphanumeric characters, alphanumeric character strings, still images, video streams, and/or three-dimensional video presentations may be included as feedback. For instance, the video streams may include customizable pre-recorded video segments as part of the feedback. In addition, the three-dimensional video representations may include a 360-degree view of a movement or a position (e.g., for spinning in ice hockey or figure skating), where a single plane is captured with an athlete facing in four directions while manipulating a margin of error.

In another embodiment, the one or more feedback devices 122 include one or more audial devices 140. For example, the one or more audial devices 140 may include, but are not limited to, a speaker, beeper, siren, an audio alarm, or other similar device capable of emitting an audible noise. For instance, the one or more audial devices 140 may be configured to output one or more of a beep, siren, alarm, an audio stream, an audio overlay message superimposed on an audio stream, and/or other audial output. Customizable audio streams may be included as audial feedback. For example, the customizable audio streams may provide pre-recorded crowd cheers to be optionally used at the end of successful repetitions or sessions.

In another embodiment, the one or more feedback devices 122 include one or more haptic devices 142. For example, the one or more haptic devices 142 may include, but are not limited to, a vibrating motor, a linear actuator, a thermal device, focused ultrasound beams, or other similar device capable of producing a physical sensation that can be sensed by the wearer.

In another embodiment, the one or more feedback devices 122 include one or more kinetic devices 144. For example, the one or more kinetic devices may include, but are not limited to, a torque motor or kinetic actuators, kinetic motors, a directed feedback device (e.g., as discussed further herein), or other device capable of imparting a direct force on the user or imparting a perceived direction on the wearer, enabling the wearer to "feel" where the desired position is located.

It is noted herein the one or more visual devices 138, the one or more audial devices 140, the one or more haptic devices 142, and/or the one or more kinetic devices 144 may be considered event-responsive (e.g., configured to deploy feedback in response to a specific signal or triggering event), for purposes of the present disclosure.

In another embodiment, at least some of the one or more feedback devices 122 may be temporally-synchronized. Temporal synchronization may occur when multiple sensors 120 simultaneously track continuous movements along/in multiple planes of movement. As movement along a particular plane continues, feedback may be emitted. For example, the feedback may vary in response to the proximity of the movement along the particular plane as the movement advances toward a target area or position. When all movements along/in all movement planes are positioned within respective target areas or positions, the feedback may converge. For example, where the feedback is a separate tone for each movement, the tones may converge to a harmonious pitch or resonant frequency. For instance, a default margin of error for the synchronization may be one standard of deviation on each side of the mean relative to the target. In addition, the margin of error may be dependent on a timing of hips and/or shoulders. In this regard, the feedback is synchronized to multiple planes that occur over time as the measured area or position approaches the desired target area or position.

It is noted herein the system 100 may include any number or combination of feedback devices 122, for purposes of the present disclosure.

In one embodiment, the system 100 includes the one or more external monitoring devices 104. The one or more external monitoring devices 104 may be used in conjunction with the KAT 102 in order to gather additional data.

The one or more external monitoring devices 104 may include, but are not limited to, one or more sensor devices not physically located on or couplable to the KAT 102, but which may be communicatively coupled into the operation of the KAT 102 to assist in developing the feedback response. For example, the one or more external monitoring devices 104 may include, but are not limited to, in-shoe pressure sensor devices, calorie intake measurement devices, eye tracking devices, external sleep monitoring devices which may collect data over a previous time (e.g., the previous night, or the like), electrocardiogram (ECG or EKG) units, electromyography (EMG) units, electroencephalogram (EEG) units for monitoring brain waves, or the like. It is noted herein the one or more external monitoring devices 104 may be communicatively coupled to the KAT 102 via wireless or wired connections.

In one non-limiting example, the external monitoring device 106 may be used to measure the angle between two joints on a human body. In this example, the external monitoring device 106 may include a potentiometer, a sensor plate, and a remote extensible reference rod. The potentiometer is mounted to the sensor plate, while the remote extensible reference rod is connected to the potentiometer such that the potentiometer forms a pivot point between the sensor plate and the remote extensible reference rod. For example, the potentiometer may be a rotary potentiometer or a linear potentiometer. A high precision analogue to digital converter (ADC) may be dedicated to reading the analog values of the potentiometer and converting the analog values to digital values that may be interpreted by the controller 108.

In another non-limiting example, the external monitoring device 106 may be used to measure ECG/EKG or EMG inputs. In this example, the external monitoring device 106 may include one or more electrodes. Each of the one or more electrodes is placed onto the user's body in the desired location. For example, the one or more electrodes include a first electrode (A), a second electrode (B), and a third electrode (REF). The first electrode and the second electrode may be placed around the muscle which activity is being measured, while the third electrode may be placed on the bone. A high quality, low-noise differential amplifier may be used to amplify or rectify the signals received from the one or more electrodes, such that the signals are readable by the ADC.

The one or more external monitoring devices 104 may be active devices with a controller including components such as, but not limited to, processors, memory, or the like. It is noted herein the components and/or the functions of the controller 108 may be considered as applicable to the components and/or the functions of the controller of the one or more external monitoring devices, for purposes of the present disclosure.

The one or more external monitoring devices 104 may be passive devices configured to transmit information and/or activate only in response to a signal from the KAT 102, the one or more external computing devices 106, or the like. For example, the one or more external monitoring devices 104 may include, but are not limited to, one or more near-field communication (NFC) devices.

In one embodiment, the system 100 includes the one or more external computing devices 106. In another embodiment, an external computing device 106 includes a controller 146. The controller 146 may be communicatively coupled with any of the components of the system 100 including, but not limited to, the KAT 102, the one or more external monitoring devices 104, or the like via one or more communication interfaces 148. For example, the one or more communication interfaces 148 may include a wireline (e.g., copper wire, fiber optic cable, wired port, or the like) or wireless connection (e.g., RF coupling, IR coupling, data network wireless communication (e.g., Wi-Fi, WiMAX, Bluetooth, 3G, 4G, 4G LTE, 5G, or the like), near-field communication (NFC), or the like).

The controller 108 may include one or more processors 150 configured to execute program instructions maintained on memory 152 (e.g., a memory medium, memory device, or the like). The one or more processors 150 of the external computing device 106 may execute any of the various process steps described throughout the present disclosure. For example, the one or more processors 150 of the controller 146 may be configured to perform one or more of capturing a set of reference data with one or more sensors, receiving an impact level and a response range of the one or more sensors, analyzing the set of reference data based on the impact level and the response range of the one or more sensors, generating a target response based on the analysis of the set of reference data, capturing a set of training data with the one or more sensors, analyzing the set of training data based on the impact level and the response range of the one or more sensors, generating a position response based on the analysis of the set of training data, comparing the position response to the target response, generating a response value based on the comparison of the position response to the target response, generating a response signal if the response value is within a configurable feedback threshold, providing the response signal to one or more feedback devices, receiving one or more additional inputs from one or more external monitoring devices, combining the one or more additional inputs and the set of reference data, transmitting the impact level and the response range for the one or more sensors to the KAT 102, receiving the impact level and the response range for the one or more sensors from the KAT 102, storing the impact level and the response range for the one or more sensors with a personal identifier, receiving one or more additional inputs from one or more external monitoring devices, combining the one or more additional inputs and the set of training data, and/or receiving the set of training data from the KAT 102. It is noted herein the controller 146 may be configured with one or more feed forward or feedback control loops for modification of the various process steps described throughout the present disclosure.

It is noted herein the communicative coupling between the communication interface 110 of the KAT 102 and the communication interface 148 of the external computing device 106 (e.g., either directly communicatively coupled, or indirectly communicatively coupled via a server, third-party external computing device, or the like) may allow for the separation of the user and wearer over a linked, wired, or wireless connection. For example, the KAT 102 and the external computing device 106 may be proximate to one another (e.g., in the same room, building, or other near-range proximity). By way of another example, the KAT 102 and the external computing device may be separate from one another (e.g., in different buildings, in different cities, states, countries, or other far-range distance).

It is noted herein the communicative coupling may allow for a user to be anywhere in the world while being able to connect to a wearer using the KAT 102. This would allow the user to coach anywhere that has an internet connection or equivalent communication channel. For example, the KAT 102 may transmit to a third-party screen-casting application, which then may transmit to an external computing device 106. The wearer (e.g., athlete) may contact the user (e.g., coach) through a video-streaming service. The wearer may assign remote control capabilities to the user, so the user may control the feedback parameters on the wearer from wherever they are while watching the wearer perform the movements and/or positions via the video-streaming service. In this regard, the system 100 allows for control between remote devices (e.g., mobile devices, or the like).

In another embodiment, the controller 146 may be configured to store and/or run KAT application software 158. For example, the KAT application software 158 may be an interface through which the user may communicate information about what practice sessions are intended for a wearer. For instance, the information may include setup information such as, but not limited to, margin of error, number of repetitions desired, and other operational parameters. By way of another example, the KAT application software 158 may be an interface through which the user may receive the results of the setups, practice, and sessions. For example, the results may be in a form including, but not limited to, videos, illustrations, numerical outputs, table summaries of data, and graphic pie charts, or the like. It is noted herein the results in any form may be sent, submitted, or uploaded to a server to allow for recall, review, and analysis at any day or time of day. For example, the server may be accessible via a web browser or web-based application.

In another embodiment, the controller 146 may be configured to store and/or run a context engine 160. For example, the context engine 160 may be configured to deliver multiple high-level commands to create different modes of operation. The context engine 160 is described in detail further herein with respect to at least FIG. 2.

It is noted herein the one or more external computing devices 106 may be in direct communication with at least the KAT 102, or may be a server through which a separate external computing device 106 configured to store and/or run the KAT application software 158 and/or the context engine 160 may be routed.

In another embodiment, a user interface 154 is communicatively coupled to or integrated with the controller 146. For example, the user interface 154 may include a display used to display data of the system 100 to a user. In another embodiment, one or more user input devices 156 are communicatively coupled to or integrated with the controller 146.

The one or more processors 112, 150 may include any processor or processing element known in the art. For the purposes of the present disclosure, the term "processor" or "processing element" may be broadly defined to encompass any device having one or more processing or logic elements (e.g., one or more micro-processor devices, one or more application specific integrated circuit (ASIC) devices, one or more field programmable gate arrays (FPGAs), or one or more digital signal processors (DSPs)). In this sense, the one or more processors 112, 150 may include any device configured to execute algorithms and/or instructions (e.g., program instructions stored in memory). In one embodiment, the one or more processors 112, 150 may be embodied as a desktop computer, mainframe computer system, workstation, image computer, parallel processor, networked computer, or any other computer system configured to execute a program configured to operate or operate in conjunction with the system 100, as described throughout the present disclosure.

The memory 114, 152 may include any storage medium known in the art suitable for storing program instructions executable by the associated one or more processors 112, 150. For example, the memory 114, 152 may include a non-transitory memory medium. By way of another example, the memory 114, 152 may include, but is not limited to, a read-only memory (ROM), a random-access memory (RAM), a magnetic or optical memory device (e.g., disk), a magnetic tape, a solid-state drive, a memory card (e.g., SD card, or the like), memory stick (e.g., USB flash drive, or the like), or the like. It is further noted that the memory 114, 152 may be housed in a common controller housing with the one or more processors 112, 150. In one embodiment, the memory 114, 152 may be located remotely with respect to the physical location of the one or more processors 112, 150 and the controller 108. For instance, the one or more processors 112, 150 may access a remote memory (e.g., server), accessible through a network (e.g., internet, intranet and the like).

The user interface 116 may include, but is not limited to, one or more smartphones, tablets, phablets, desktops, laptops, or the like. The display of the user interface 116, 154 may include any display known in the art. For example, the display may include, but is not limited to, a liquid crystal display (LCD), an organic light-emitting diode (OLED) based display, or a CRT display. Those skilled in the art should recognize that any display device capable of integration with a user interface 116, 154 is suitable for implementation in the present disclosure.

The one or more user input devices 118, 156 may include, but are not limited to, one or more button, toggles, switches, or the like. By way of another example, the one or more user input devices 118, 156 may include, but are not limited to, a touch pad, a touch screen, or the like. By way of another example, the one or more user input devices 118, 156 may include, but are not limited to, a microphone used to receive voice commands (e.g., start, stop, pause, restart, save, or the like) and/or data input (e.g., breathing rate, loudness of noise made while moving or stepping, or the like). In another embodiment, a wearer may input selections and/or instructions responsive to data displayed to the wearer via a user input device 118, 156 of the user interface 116, 154.

Figure 2:
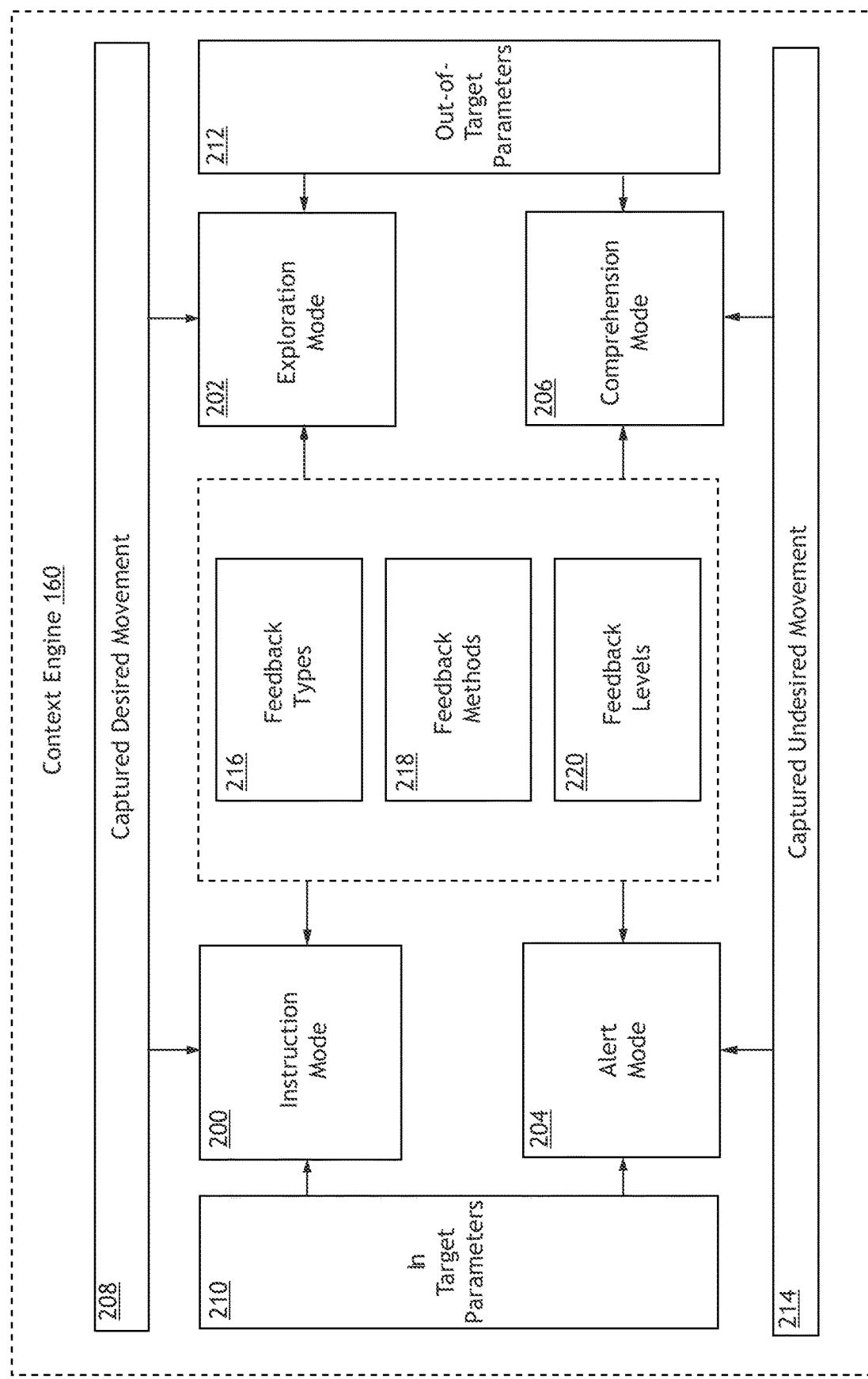
FIG. 2 illustrates a simplified block diagram illustrating a portion of a system for providing kinesthetic awareness, in accordance with one or more embodiments of the present disclosure.

FIG. 2 illustrates a simplified schematic of the context engine 160 of the controller 146 of the external computing device 106, in accordance with one or more embodiments of the present disclosure.

In one embodiment, the context engine 160 is configured to operate in one or more context modes (e.g., training modes according to pedagogical frameworks). For example, the one or more modes may include, but are not limited to, an Instruction mode 200 (e.g., "Learning", "Correction"," Cognitive", or "Deliberative" mode), an Exploration mode 202 (e.g., "Awareness" or "Associative" mode), an Alert mode 204 (e.g., "Habit Recognition" or "Habit Break" mode), and/or a Comprehension mode 206 (e.g., "Habit Comprehension" or "Exaggerated Mistake" mode). In another embodiment, each mode may carry context information about the direction of feedback. For example, feedback may be supplied when the training data (e.g., an action) is "In" a desired target range. By way of another example, feedback may be continually supplied while training data indicates the training data is "Out" of a desired target range. In another embodiment, the context may be defined by the user and may be responsive to a wearer's movement and the user's objective for the session. In another embodiment, depending on the mode the KAT application software 158 may manage the various modes by relying on inputs from the KAT 102 and issuing a series of high-level commands to the controller 108. The controller 108, in turn, controls the one or more sensors 120 and one or more feedback devices 122.

In another embodiment, the instruction mode 200 focuses on "Good" or desired movements 208 captured with the KAT 102. The instruction mode 200 represents a general method to teach and reinforce specific movement patterns, associating a desired technique with one or more stimuli as feedback presented after the desired technique occurs (e.g., positive reinforcement, or the addition of a positively associated stimuli). For example, the feedback type is set to "In", so that feedback is delivered when the training data is "In" (e.g., when the desired movements 208 are within a range of in-target parameters 210) and the "Good" position is achieved. The instruction mode 200 informs a wearer when the right position is being performed so that the wearer can explore their sensorimotor space to understand the desired movement, identifying and understanding the sensation of desired patterns by offering instructions when the desired movement is replicated.

In another embodiment, the exploration mode 202 focuses on "Good" or desired movements 208 captured with the KAT 102. The exploration mode 202 represents a general method to teach and reinforce against specific movement patterns, associating the desired technique with one or more stimuli as feedback presented until the desired technique occurs (e.g., negative reinforcement-the removal of a negatively associated stimuli). For example, the feedback type is set to "Out", so that feedback is delivered when the training data is "Out" (e.g., when the desired movements 208 are outside the range of in-target parameters 210, but within a range of out-of-target parameters 212) until the "Good" position is achieved, at which time the feedback ceases. The exploration mode 202 informs a wearer when the right position is not being performed so that the wearer can explore their sensorimotor space to understand the movement necessary to perform the desired movement, identifying and understanding the sensation of desired patterns by offering the instructions until the desired movement is replicated.

In another embodiment, the alert mode 204 focuses on "Bad" or un-desired movements 214 captured with the KAT 102. The alert mode 204 represents a general method to teach and reinforce against specific movement patterns, associating the un-desired technique with one or more stimuli as feedback presented while the un-desired technique occurs (e.g., positive reinforcement). For example, the feedback type is set to "In", so that feedback is delivered when training data is "In" (e.g., when the un-desired movements 214 are within a range of in-target parameters 210) and the "Bad" position is achieved. The break habit mode 204 informs a wearer when the wrong position is performed so that the wearer can explore their sensorimotor space to understand when they are incorrect, identifying and understanding the sensation of deeply-encoded, un-desired patterns by offering the instructions when the un-desired movement is replicated.

In another embodiment, the comprehension mode 206 focuses on "Bad" or un-desired movement 214 captured with the KAT 102. The comprehension mode 206 represents a general method to teach and reinforce against specific movement patterns, associating the un-desired technique with one or more stimuli as feedback presented until the un-desired technique occurs (e.g., negative reinforcement). For example, the feedback type is set to "Out", so that feedback is delivered when the training data is "Out" (e.g., when the desired movements 208 are outside the range of in-target parameters 210, but within a range of out-of-target parameters 212) until the "Bad" position is achieved, at which time the feedback ceases. The comprehension mode 206 allows a wearer to explore their sensorimotor space to understand and/or experience the wrong position so that the wearer understands what they are doing incorrectly, identifying and understanding the sensation of deeply-encoded, un-desired patterns by offering the least-specific instructions until the un-desired movement is replicated.

For purposes of the present disclosure, "positive reinforcement" refers to the addition of a pleasant factor, "positive punishment" refers to the addition of an unpleasant factor, "negative reinforcement" refers to the removal or withholding of an unpleasant factor, and "negative punishment" refers to the removal or withholding of a pleasant factor.

In another embodiment, the KAT 102 provides feedback for one or more same or different types of movements. For example, the movements may include continuous skills such as, but not limited to, rhythmic walking, running, or the like. By way of another example, the movements may include discreet skills such as, but are not limited to, throwing, swinging, sitting, or the like. By way of another example, the movements may include, but are not limited to, open skills which are dependent on the environment and/or task constraints. By way of another example, the movements may include, but are not limited to, closed skills which are pre-determined and not dependent on the environment and/or task constraints.

In another embodiment, the varying range of feedback necessary to respond to the one or more same or different types of movements may result in one or more same or different feedback types 216, feedback methods 218, and/or feedback levels 220 being employed.

The feedback types 216 may include, but are not limited to, visual feedback via the one or more visual devices 138, auditory feedback via the one or more audial devices 140, haptic feedback via the one or more haptic devices 142, kinetic feedback via the one or more kinetic devices 144, or the like.

The feedback methods 218 may include, but are not limited to, binary feedback, gradual feedback including proportional feedback, guidance feedback including gradient feedback, assessment feedback, on-request feedback, directed feedback, or other types of feedback which may be used or beneficial during motor learning (e.g., an acquiring or changing of a movement or position).

For example, if binary feedback is generated the strength of the feedback may be set to either 0% or 100%.

By way of another example, if gradual feedback is generated the magnitude of the feedback level 220 may be proportional to the calculated strength of a numerical response and tracked/modulated using a proportional-integral-derivative (PID) loop (e.g., a three-term loop, though two- or one-term loops may also be used) with a non-zero derivative term allowing for rapid response and smooth, natural transitioning.

By way of another example, if guidance feedback is generated PIDs are used to modulate the gyroscopic motors, or other kinetic device, depending on how far away the KAT 102 is from the target position, and offers adjustable types of feedback in any combination of feedback types 216. For example, gradient (gradually changing) vibrating sensations, frequency of tone, louder or softer volume variations, sine wave sounds, square wave sounds, and other sounds when the KAT 102 moves further towards or moves further away from the target position. The use of gyroscopes allows the KAT 102 to provide an intuitive "guidance" sensation to the user which enables the user to "feel" where the target position is located. It is noted herein a determination of "how far away", and "moves further toward or moves further away" may be dependent on a magnitude of difference between an actual movement or position value versus a target movement or position value.

By way of another example, assessment feedback may be used to evaluate performance. Assessment feedback may deliver no feedback during a set of repetitive movements until the last few of the repeated movements of the set. It is noted herein the wearer may set the number of repetitions and/or the sequence to receive feedback.

By way of another example, on-request feedback may be used to evaluate performance. On-request feedback may delay (e.g., not provide) feedback during practice, although the feedback or response signal is collected and may be supplied at any time during the practice, until requested by the wearer. For example, the feedback or response signal may be requested (e.g., via a gesture on or proximate to the KAT 102) on an as-needed basis during or after the practice, and the KAT 102 may return immediate feedback about the last repetition. It is noted herein a gesture on or proximate to the KAT 102 may be configured to cause the KAT 102 to retroactively capture, label, and store (or transmit) a previous position or movement.

It is noted herein the various feedback methods as listed and discussed above are issued or invoked as a response to something (e.g., response to a target being reached, response to a performance level being attained, or the like).

By way of another example, directed feedback both responds to a target being obtained and provides a suggestion in the form of directional information through the one or more feedback devices 122. The one or more feedback devices 122 may include, but are not limited to, kinetic motors which stimulate mechanoreceptors in the skin. It is noted herein mechanoreceptors form a class of somatosensory receptors whose function is to relay extracellular stimulus to intracellular signal transduction through mechanically gated ion channels. More specifically, mechanoreceptors such as Merkel's disk are slow-adapting unencapsulated nerve endings that respond to light touch, and are present in the upper layers of skin that have hair or are glabrous. In addition, mechanoreceptors such as Ruffini endings are responsive to skin stretch. Further, mechanoreceptors such as Pacinian corpuscles are rapidly adapting, deep receptors that respond to deep pressure and high frequency vibrations. The external stimuli used to stimulate mechanoreceptors may be in the form of touch, pressure, stretching, sound waves, and/or motion, or other types of stimuli a kinetic motor would be capable of providing. For example, activating feedback devices 122 set in a particular pattern (e.g., circle, in sequence along a line, or the like) within the KAT 102 may create the sensation, impression, or illusion of movement in a specific direction. By way of another example, activating the feedback devices 122 at different frequency levels may create the sensation of movement in a specific direction. For instance, driving the kinetic feedback devices at different frequency levels may create the sensation, impression, or illusion of movement in a specific direction. In addition, pulsing an LED (Light Emitting Diode set in a particular pattern (e.g., a circle, in sequence along a line, or the like) may cause the human eye to sense the optical illusion of motion. Further, where the KAT 102 includes multiple audial devices 140, the placement and/or directionality of the audial devices 140 and the delay in different feedback sounds at different times (e.g., as left versus right sounds), may create sensation, impression, or illusion of movement due to the doppler effect and human audio localization.

It is noted herein an array of kinetic motors usable as feedback devices 122 may be fastened to a wearer (e.g., on the skin of a wearer's back, or the like). For example, the array of kinetic motors may be positioned at select locations within the KAT 102 and/or on the wearer at select locations external to and proximate to the KAT 102. For instance, the array of kinetic motors may be defined by directional or coordinate positions within at select locations within the KAT 102 and/or on the wearer at select locations external to and proximate to the KAT 102, such that activation of a kinetic motor corresponds to a particular direction or coordinate position the wearer should adjust toward or away from (e.g., which may be dependent on the mode 200, 202, 204, 206 currently in use).

In one non-limiting example, the KAT 102 may be worn by a soccer or football player, and used by a coach to adjust the player toward or away from a particular direction or coordinate position on the field or pitch. In this example, the player may be adjusted toward a teammate (e.g., if having drifted too far away outside of the defender line or forward line), adjusted away from an opponent (e.g., if the opponent is able to outpace the player), adjusted away from a potential off-sides penalty, or the like. The adjustment may be accomplished through activation of particular kinetic motors indicating one or more directions (e.g., simultaneous or sequential adjustments, in the case of multiple directions) the player should adjust. The adjustment by the coach may dynamic (e.g., during gameplay) or static (e.g., during drills) The kinetic motors which comprise the array are selectively activated to provide a computer-simulated kinesthetic direction indicator, such that the player can feel the movement that is desired.

In another non-limiting example, the KAT 102 may be worn by a baseball player, and used by a coach to adjust the player within a batter's box. In this example, the player may be directed toward or away from the pitcher in the box, toward or away from the plate in the box, into or out of a bunting stance, or the like. The adjustment may be accomplished through activation of particular kinetic motors indicating one or more directions (e.g., simultaneous or sequential adjustments, in the case of multiple directions) the player should adjust. The adjustment by the coach may dynamic (e.g., during gameplay) or static (e.g., during hitting practice). The kinetic motors which comprise the array are selectively activated to provide a computer-simulated kinesthetic direction indicator, such that the hitter can feel the movement that is desired.

In another non-limiting example, the KAT 102 may be worn by a golfer, and used by a coach or by the wearer themselves (e.g., with pre-programmed instructions) to adjust the golfer in a tee box. In this example, as the golfer prepares and queues up to swing a golf club, one or more selective motor activations to guide the wearer to the desired club swing. The kinetic motors which comprise the array are selectively activated to provide a computer-simulated kinesthetic direction indicator, such that the golfer can feel the movement that is desired.

It is noted herein a feedback method 218 for the Instruction mode 200, the Exploration mode 202, the Alert mode 204, and/or the Comprehension mode 206 may include, but is not limited to feedback methods of binary, gradient, random, or on-request.

It is noted herein some of the one or more feedback methods 218 may have only one magnitude (e.g., on/off), while other feedback methods 218 have discrete levels (e.g., specific colors of a select number of lights such as red/yellow/green, or the like), while other feedback methods 218 may have a range of levels (e.g., sound levels of a beeper, frequencies of vibrations, or the like).

Whether the one or more feedback methods 218 have one magnitude, discrete levels, or a range of levels, the feedback levels 220 may include, but are not limited to, dose, duration, frequency, intensity, or the like. For example, dose is a measured quantity of the feedback delivered at one time. By way of another example, duration is a time during which the feedback occurs and continues. By way of another example, frequency is a rate at which the feedback occurs. By way of another example, intensity is a condition of strength, energy, concentration, or the like of the feedback.

It is noted herein the system 100 may include any number or combination of feedback types 216, feedback methods 218, and/or feedback levels 220, for purposes of the present disclosure.

Figure 3A:
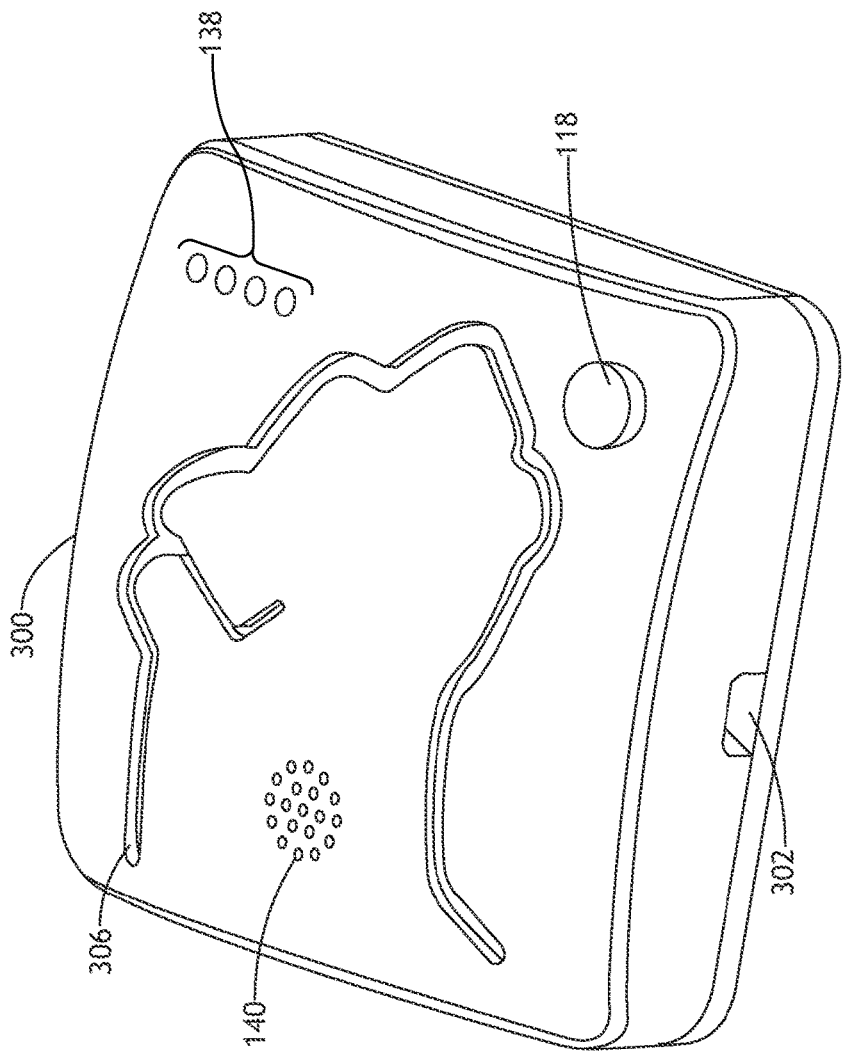
FIG. 3A illustrates a kinesthetic awareness tool of a system for providing kinesthetic awareness, in accordance with one or more embodiments of the present disclosure.
Figure 3B:
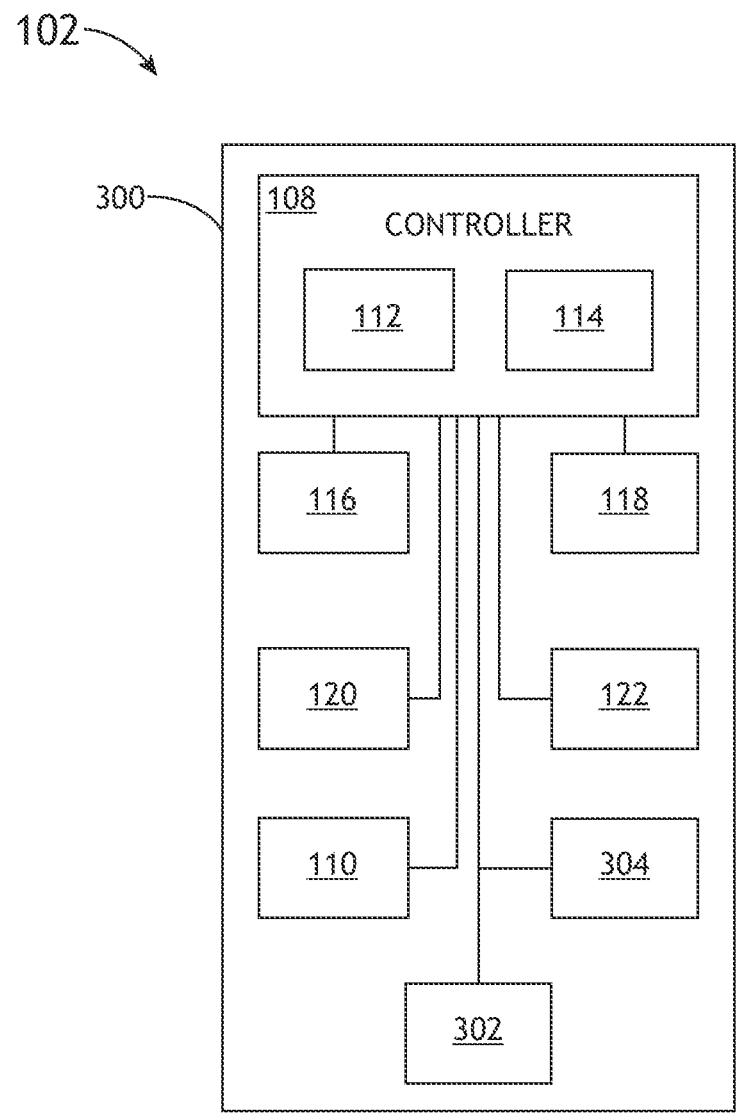
FIG. 3B illustrates a simplified block diagram of a kinesthetic awareness tool of a system for providing kinesthetic awareness, in accordance with one or more embodiments of the present disclosure.

FIGS. 3A and 3B illustrates example embodiments of the KAT 102, in accordance with one or more embodiments of the present disclosure.

In one embodiment, the KAT 102 includes a housing 300. One or more components of the KAT 102 (e.g., as illustrated in FIG. 1 and described throughout the present disclosure) may be mounted within the housing 300, pass through an exterior surface of the housing 300, or be mounted to the exterior surface of the housing 300. For example, the controller 108, the communication interface 110, the one or more sensors 120, and the one or more feedback devices 122 may be mounted within the housing 300.

The housing 300 may be configured with an attachment mechanism, allowing the KAT 102 to be readily attached to the wearer. For example, the attachment mechanism may include the use of hook and loop fasteners, straps, an adhesive, or the like. In other embodiments, the housing may be configured to be fit and contained within a specialized pocket or seamed area (e.g., a cuff or pocket that may be sewn shut during manufacturing) on the user's clothing.

In another embodiment, the KAT 102 may use a wired connection to draw current from a power source. For example, the KAT 102 may include one or more ports 302 that are integrated into the housing 300, electronically connected to the controller 108, and electrically connected to a battery 304. The one or more ports 302 may be configured for performing a number of functions, including but not limited to, charging the battery, connecting the external monitoring device, connecting an external storage device (e.g., a secure digital (SD) card, universal serial bus (USB) drive, or the like), or the like.

In another embodiment, the KAT 102 may include the battery 304 installed within the housing 300. The battery 304 may supply current to the one or more components of the KAT 102 including, but not limited to, the controller 108, the one or more sensors 120, the one or more feedback devices 122, or the like. The battery may be non-rechargeable or rechargeable.

In another embodiment, the KAT 102 may include the one or more user input devices 118. The one or more user input devices 118 may be integrated into the housing 300. Basic, intuitive user interaction is ensured by ergonomic placement of the one or more user input devices 118 about the housing 300. For example, the one or more user input devices 118 may allow the user to adjust parameters of the one or more sensors 120 and/or the one or more feedback devices 122. By way of another example, the one or more user input devices 118 may allow the user to adjust parameters of the one or more sensors 120 and/or the one or more feedback devices 122 may initiate sequences performed by the controller 108. In another embodiment, controlled parameters and/or sequences may be visible on a display screen of the KAT 102.

In another embodiment, the housing 300 may include one or more markings 306 on or partially embedded within an exterior surface. For example, the one or more markings 306 may include, but are not limited to, a company logo, a team logo, a warning label, printed instructions, Federal Communications Commission Identification (FCC ID) information, or the like.

In another embodiment, the KAT 102 may include the wired connections and/or circuitry necessary to headphone usage. For example, the headphones may provide audial feedback. For instance, the audial feedback may be provided overlaid with a wearer's music being played through the headphones. By way of another example, the headphones may be connected to the KAT 102 or the external monitoring device 106 via Bluetooth.

Figure 4A:
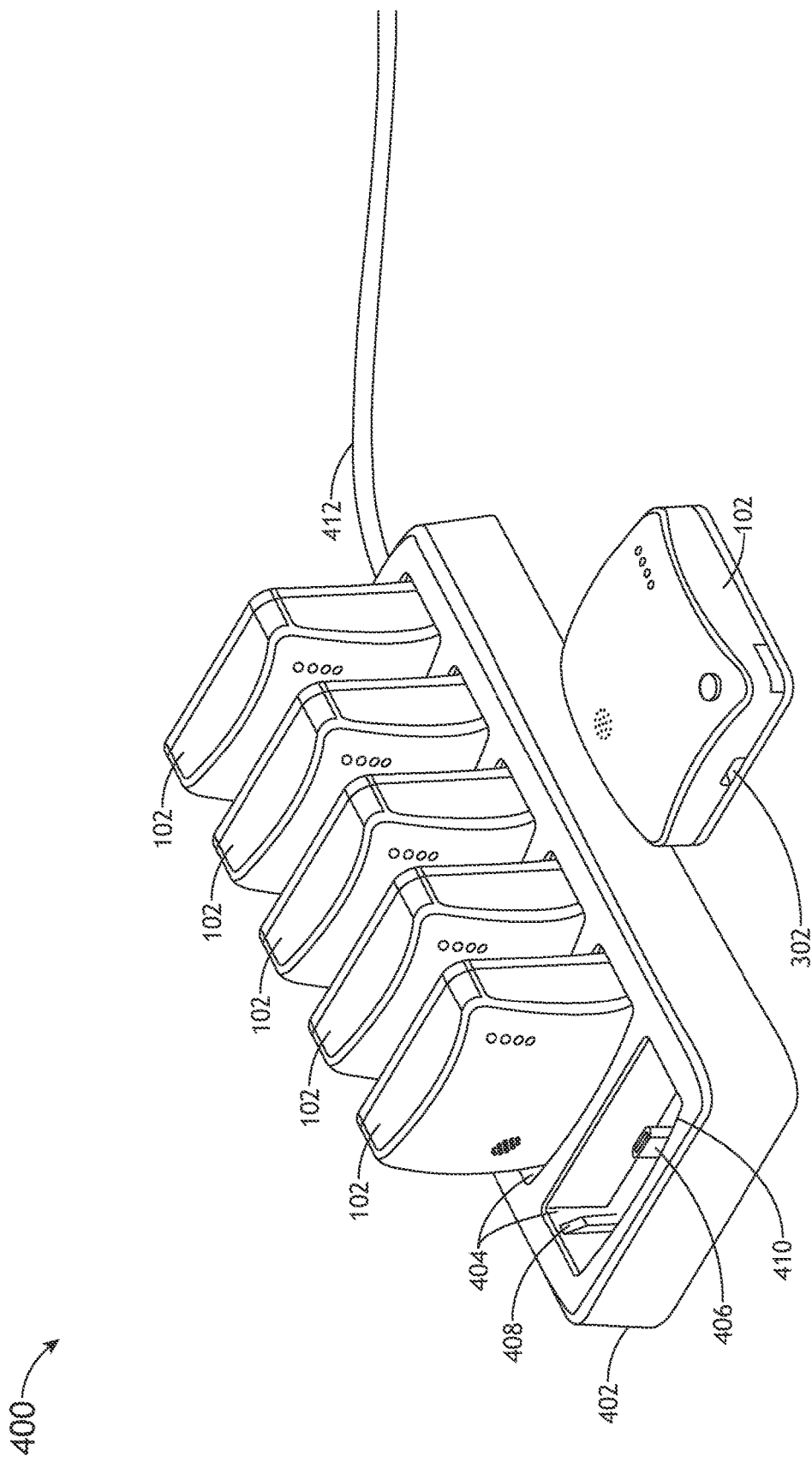
FIG. 4A illustrates a dock and kinesthetic awareness tools of a system for providing kinesthetic awareness, in accordance with one or more embodiments of the present disclosure.
Figure 4B:
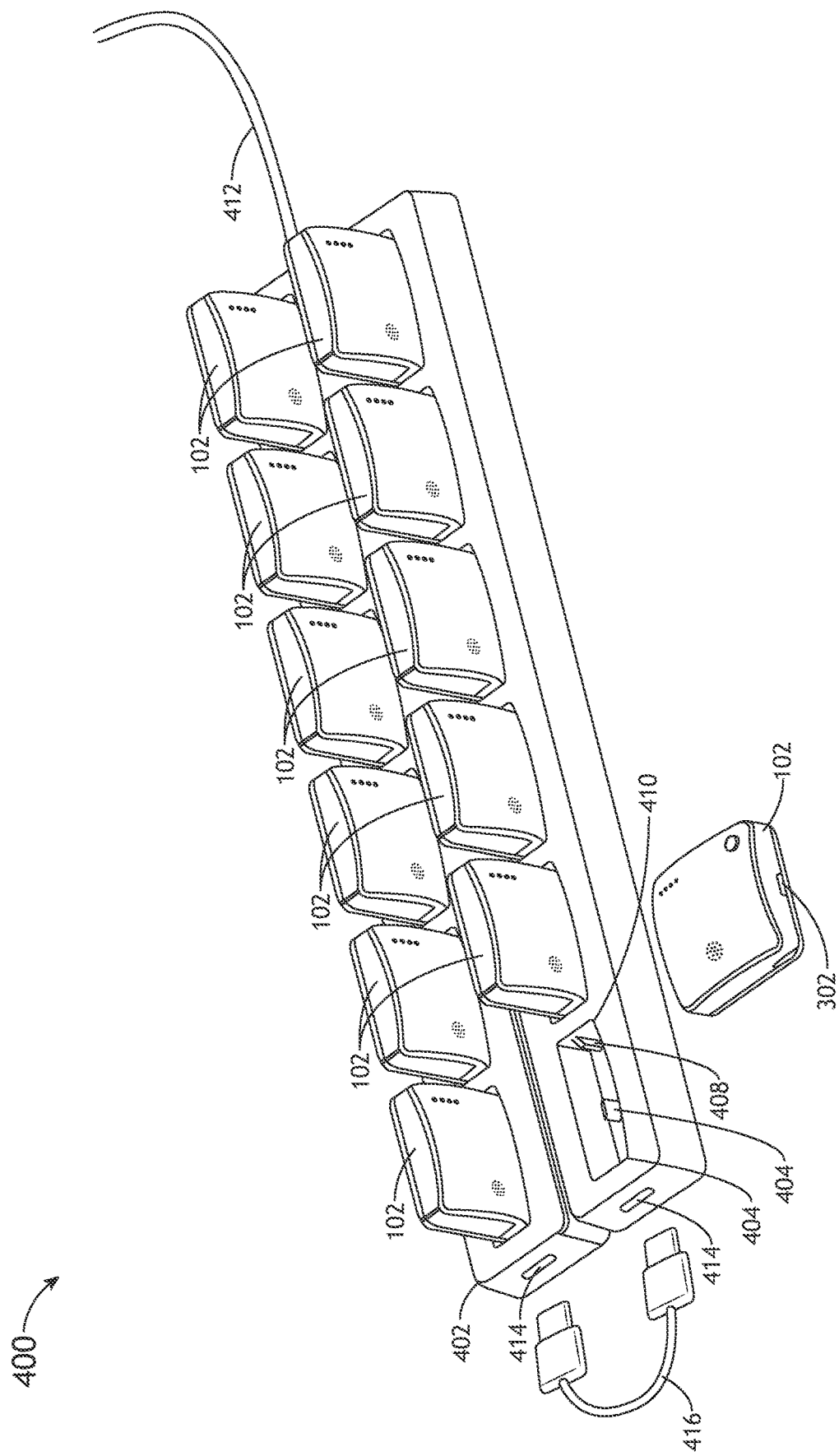
FIG. 4B illustrates multiple docks and multiple kinesthetic awareness tools of a system for providing kinesthetic awareness, in accordance with one or more embodiments of the present disclosure.

FIGS. 4A and 4B illustrate accessories for the system 100 including the KAT 102, in accordance with one or more embodiments of the present disclosure.

In one embodiment, the system 100 includes a dock 400. In another embodiment, the dock 400 includes a chassis 402 with one or more cavities 404. For example, the chassis 402 may be configured to receive and/or interact with one or more KAT 102. By way of another example, the one or more KAT 102 may be inserted into a corresponding cavity 404 defined within the chassis 402 such that a portion of the housing 300 is accessible by a user or a wearer. For example, a user or a wearer may be able to remove a KAT 102 from the chassis 402 without interfering with an adjacent KAT 102.

In another embodiment, the one or more cavities 404 may include a notch 406 configured to interact with a corresponding KAT 102. For example, the KAT 102 may have a groove that mates with the notch 406. By way of another example, the exterior dimensions of the KAT 102 may be configured to abut against the notch 406, providing a holding force against the KAT 102 in the form of friction.

In another embodiment, the chassis 402 may be configured to transfer power to (e.g., charge) the battery 304 of the KAT 102, and/or may be configured to transfer data between the KAT 102 and one or more components of the system 100 (e.g., the external computing device 106, or the like). For example, the cavity 404 may include one or more connectors 410. For example, a connector 410 may be a male end of a connector set (e.g., with the port 302 of the KAT 102 being the female end). By way of another example, the chassis 402 may include one or more inductive surfaces. It is noted herein the connector 410 may be per-KAT 102, while the inductive surfaces may be per-KAT 102 or shared by the collective KAT 102. By way of another example, the chassis 402 may include a cable 412 configured to provide a wired connection (e.g., to an external computing device 106). By way of another example, the chassis 402 may include the circuitry necessary to communicatively couple to the external computing device 106 via wireless means.

In another embodiment, the chassis 402 may be configured to a single KAT 102 or multiple KAT 102. For example, where the chassis 402 is configured to multiple KAT 102, the multiple KAT 102 may be arranged in a single row or multiple rows. For instance, the multiple rows may be in a single chassis 402. By way of another example, the multiple rows may be in multiple chassis 402, where each of the multiple chassis 402 include a port 414 couplable together via a cable 416. It is noted herein the multiple chassis 402 may be couplable together via wireless means.

FIGS. 5A-5F illustrate example pages or screens of the KAT software application 158 configured to communicatively couple to the KAT 102, in accordance with one or more embodiments of the present disclosure. FIG. 6 illustrates an example portal for the KAT software application 158 configured to communicatively couple to the KAT 102, in accordance with one or more embodiments of the present disclosure.

Figure 5A:
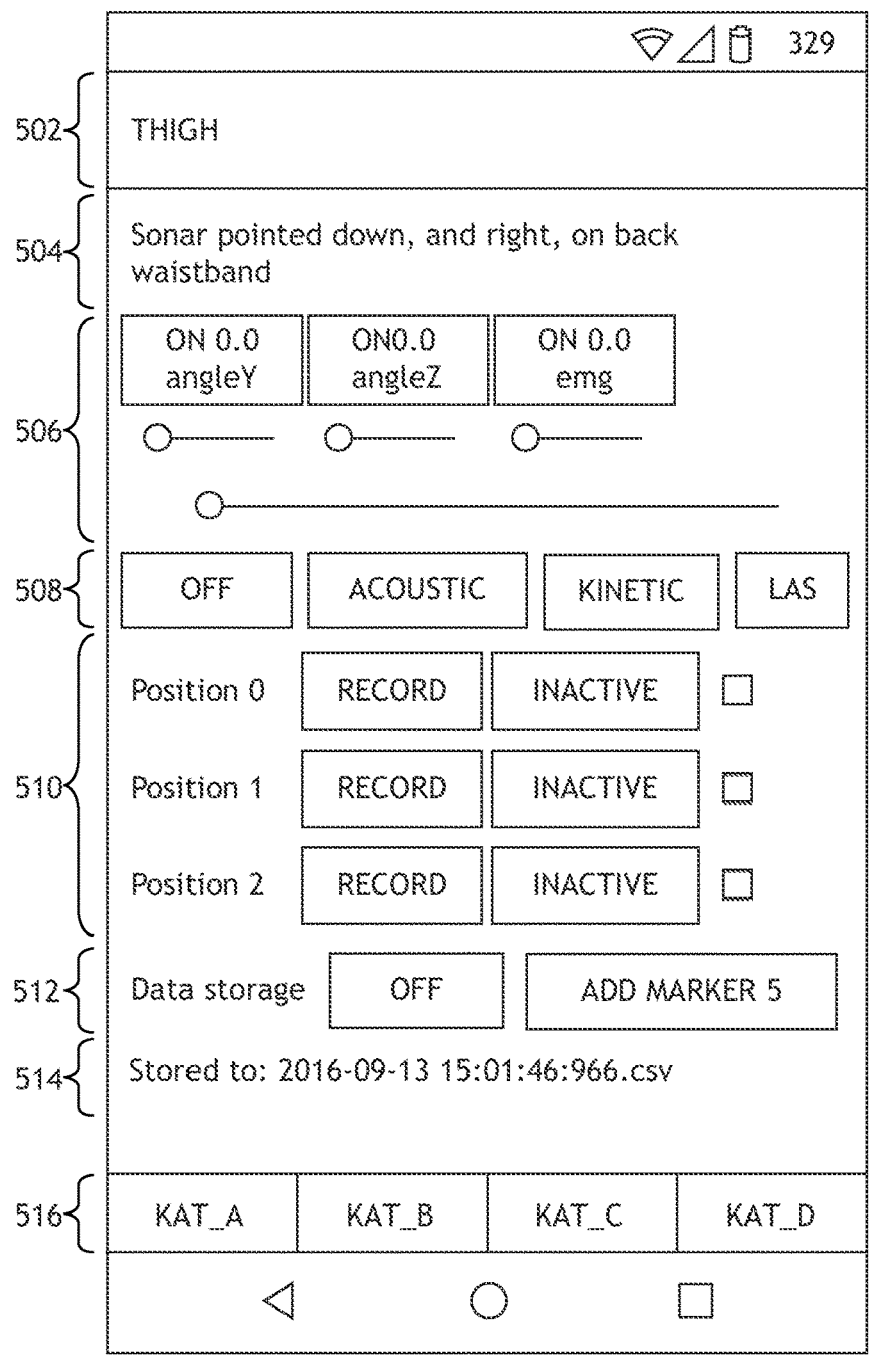
FIG. 5A is an example user interface utilized by a system for providing kinesthetic awareness, in accordance with one or more embodiments of the present disclosure.
Figure 5B:
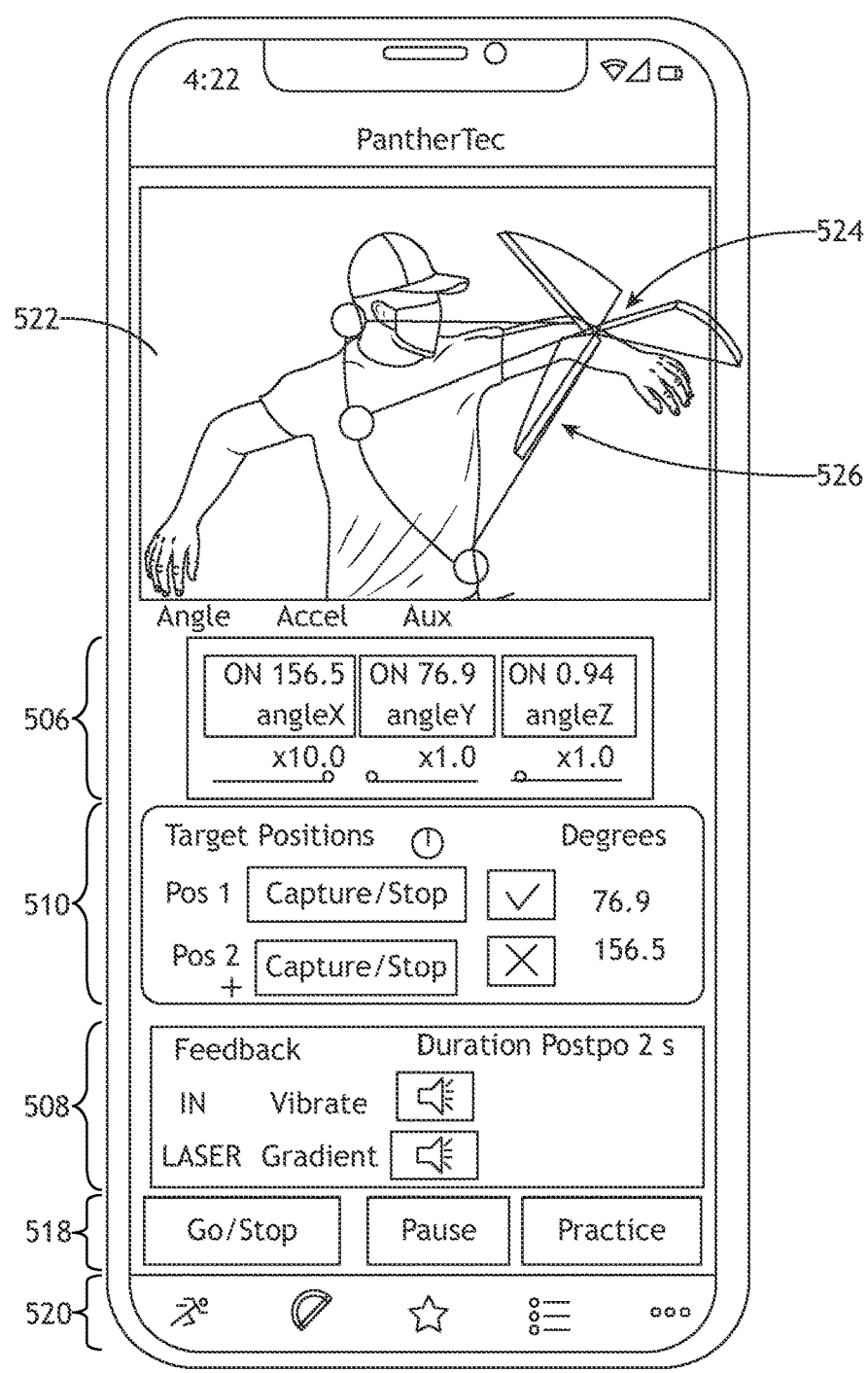
FIG. 5B is an example user interface utilized by a system for providing kinesthetic awareness, in accordance with one or more embodiments of the present disclosure.
Figure 5D:
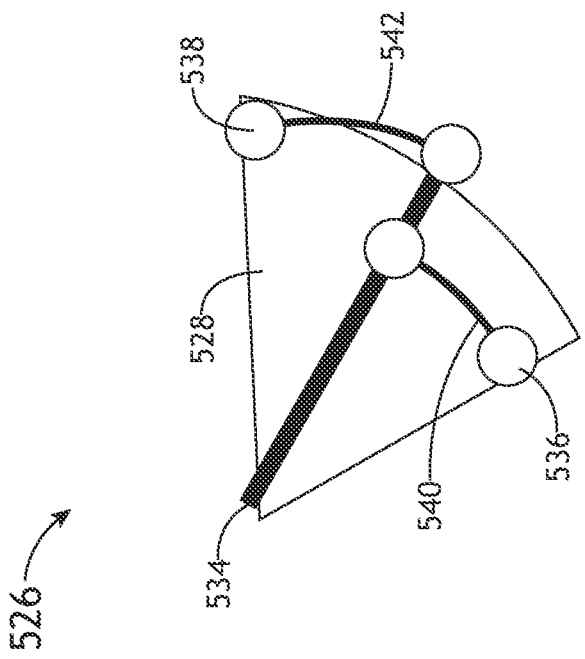
FIG. 5D is a response range icon of an example user interface utilized by a system for providing kinesthetic awareness, in accordance with one or more embodiments of the present disclosure.
Figure 5C:
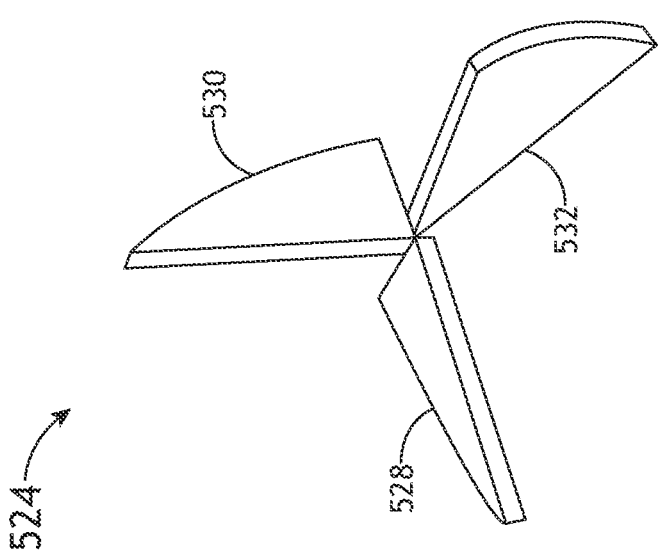
FIG. 5C is a tri axial icon of an example user interface utilized by a system for providing kinesthetic awareness, in accordance with one or more embodiments of the present disclosure.
Figure 5E:
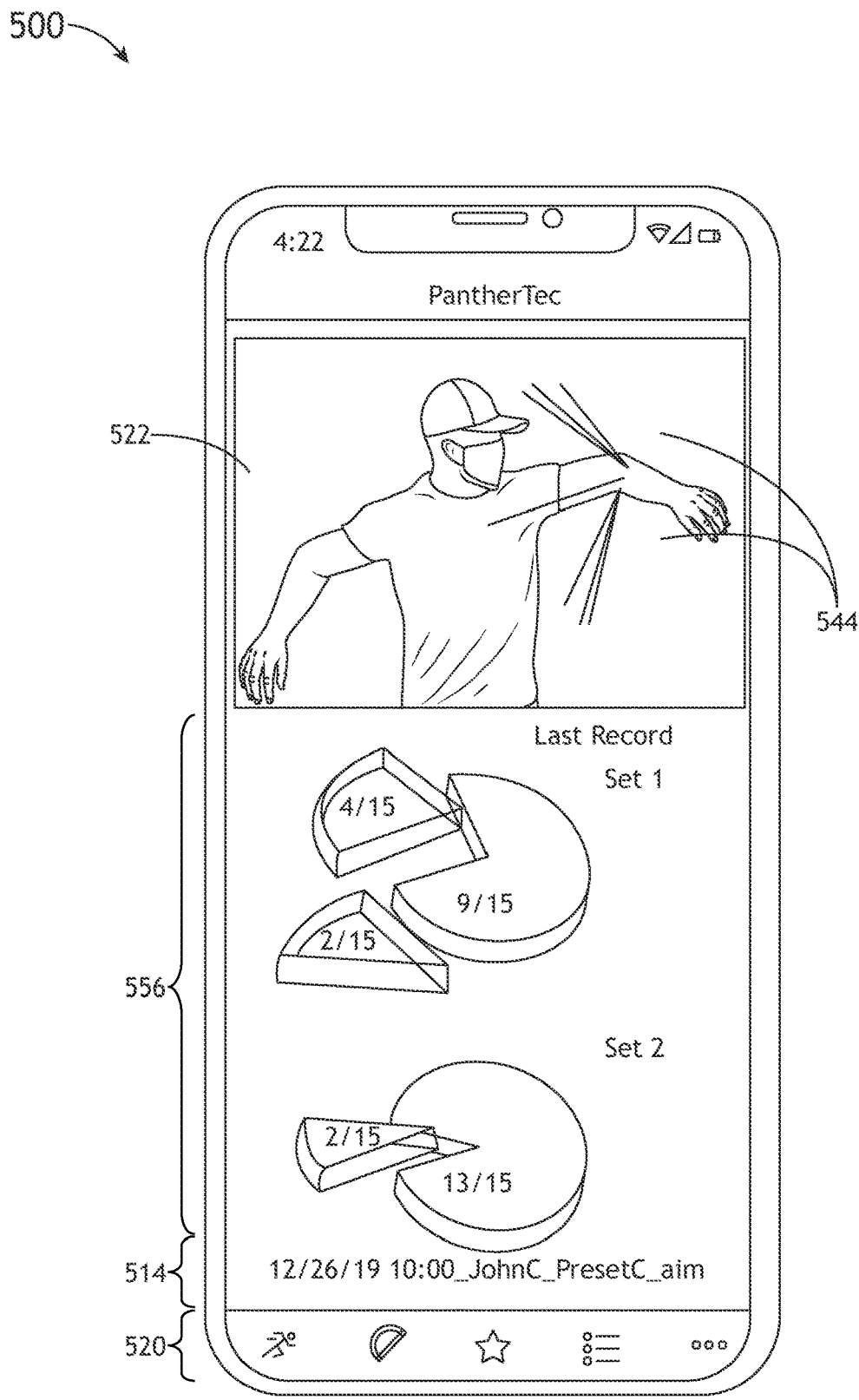
FIG. 5E is an example user interface utilized by a system for providing kinesthetic awareness, in accordance with one or more embodiments of the present disclosure.
Figure 5F:
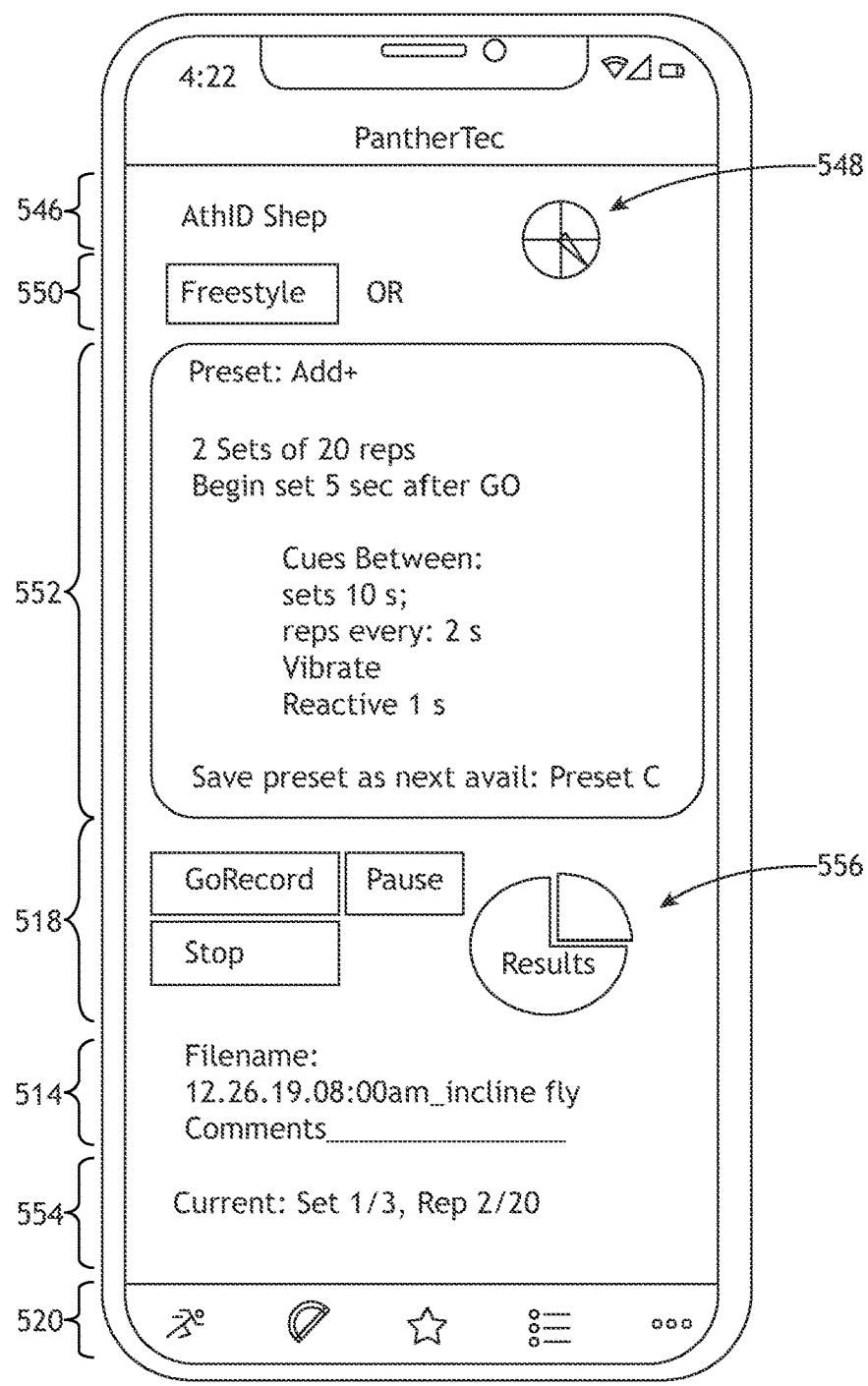
FIG. 5F is an example user interface utilized by a system for providing kinesthetic awareness, in accordance with one or more embodiments of the present disclosure.
Figure 6:
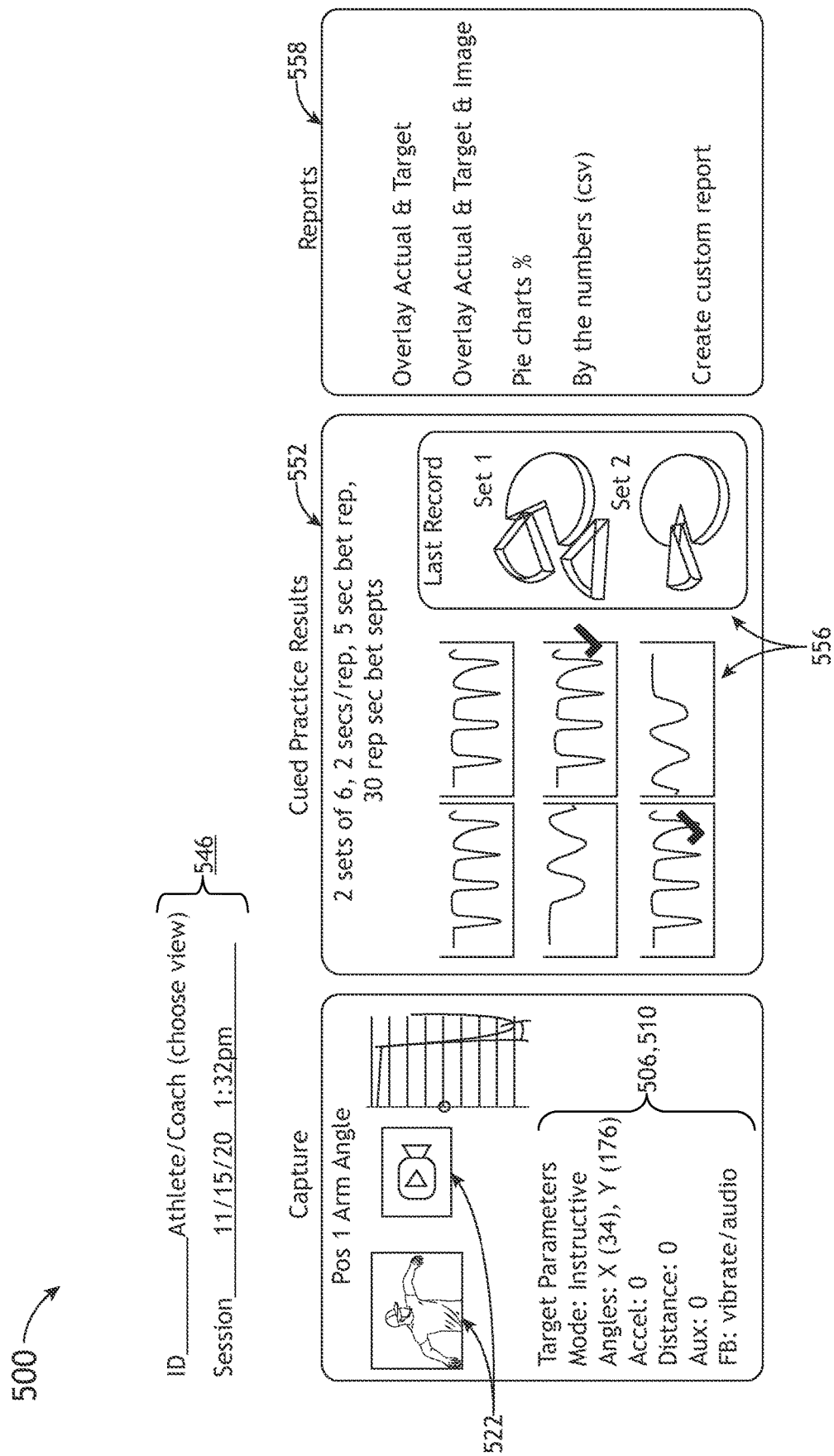
FIG. 6 is an example user interface utilized by a system for providing kinesthetic awareness, in accordance with one or more embodiments of the present disclosure.

In one embodiment, the KAT software application 158 as illustrated in FIGS. 5A-6 may be operated on the KAT 102 or the external computing device 106. For example, the external computing device 106 may include, but is not limited to, a smartphone, personal computer, server, or the like.

Referring now to FIG. 5A, the KAT software application 158 provides a user interface 500 for a wearer or a user. For example, the user interface 500 may be displayed on the user interface 116 of the KAT 102 and/or the user interface 154 of the external computing device 106.

In one embodiment, the user interface 500 may include a KAT location 502 (e.g., a location on a wearer body or tool or other localized place proximate to the wearer) and a KAT orientation 504. In another embodiment, the user interface 500 may include one or more user inputs in the form of graphical user interface (GUI) controls. It is noted herein the user interface 500 as illustrated in FIGS. 5A-6 may be taken at an instance where a capture button has been activated. For example, FIG. 5A illustrates an instance without the use of an image capture feature, where an image may be capture with a camera during the pressing of a capture button. It is noted herein, however, the above description should not be interpreted as a limitation on the scope of the present disclosure but merely an illustration.

In another embodiment, the user interface 500 may include one or more sensor GUI controls 506 configured to allow a user or wearer to monitor and adjust parameters and/or thresholds of the one or more sensors 120. For example, the one or more sensor GUI controls 506 may include a readout or toggle for type of sensor reading, one or more local adjusters (e.g., per sensor 120), one or more global adjusters (e.g., for all sensors 120), or the like. For instance, a sensor GUI control 506 may apply to any or all of the one or more sensors 120. In addition, a sensor GUI control 506 may apply to any or all the individual x, y, and z planes of each sensor 120. Further, a sensor GUI control 506 may apply to any or all the below a target value, at the target value, or above the target value.

In another embodiment, the user interface 500 may include one or more feedback device GUI controls 508 configured to allow a user or wearer to monitor and adjust feedback provided by the one or more feedback devices 122. For example, the one or more feedback GUI controls 508 may include one or more readouts or toggles for one or more feedback types 216, feedback methods 218, or feedback levels 220.

In another embodiment, the user interface 500 may include one or more capture GUI controls 510 configured to allow a user or wearer to initiate capture sessions. For example, the one or more capture GUI controls 510 may include one or more readouts or toggles for a particular type of data being captured and/or type of capture session.

In another embodiment, the user interface 500 may include one or more data recording GUI controls 512 configured to allow a user or wearer to initial data recording. For example, the one or more data storage GUI controls may include one or more toggles to activate data recording of position data in one, two, or three dimensions. For instance, the one or more toggles (e.g., "Marker") may add a marker to the position data in the form of a time stamp.

In another embodiment, targets for the wearer may be set through manual interaction with the user interface 500. For example, manually setting the targets for the wearer may include, but are not limited to, choosing numerical values from a list that populates after activating a toggle on the user interface 500, tapping a still image/graphic/video display on the user interface 500, interacting with a slider or bar by swiping on the user interface 500, drawing a movement path in a defined area on the user interface 500, typing in numeric values in a pre-populated input box or an input box that populates after activating a toggle on the user interface 500, or the like.

In another embodiment, the user interface 500 may include a data storage location 514. In another embodiment, the software application may be used to monitor different features of a particular KAT 102, providing a "tabs"-styled interface with one or more tabs 516 for managing multiple different features of the particular KAT 102, where each tab represents one or more features. In another embodiment, the software application may be used to monitor multiple KAT 102, providing a "tabs"-styled interface for managing multiple connections, where each tab represents one or more KAT 102.

Referring now to FIGS. 5B-5E, in another embodiment, the user interface 500 may include one or more session GUI controls 518. For example, the one or more session GUI controls may include one or more readouts or toggles for starting a session, stopping a session, pausing a session, or practicing a movement or position prior to running the session.

In another embodiment, the user interface 500 may include one or more application GUI controls 520. For example, the one or more application GUI controls 520 may allow a user or wearer to navigate the KAT software application 158.

In another embodiment, the user interface 500 may include a still image or video 522. For example, the still image or video 522 may be generated from a set of reference data or a set of previous training data taken of the wearer. By way of another example, the still image or video 522 may be generated from a set of reference data or a set of previous training data taken from a different wearer, where the different wearer is used as a baseline for the movement or position. It is noted herein the set of reference data may be captured in real-time, or may be captured through retroactive capturing procedures as described throughout the present disclosure.

In one non-limiting example, the still image or video 522 may be combined with measurement data so that the user or the wearer can better visualize the movement measured by the one or more sensors 120 in relation to the movement of the wearer. For example, the still image or video 522 may be taken by a phone camera as a basis for the overlay operation. The still image may be uploaded to the KAT application software 158 running as a smartphone application or computer application on the one or more external computing devices 106.

To align the graphical representation of the movement (e.g., a graphical representation of the sensor values) on the still image or video 522 showing the body's pivot point, the user or the wearer may adjust an "axial icon" 524 representing three movement planes on the user interface 116 and/or the user interface 154. For example, where the movement or position is in three or more planes, the axial icon 524 may be a tri axial icon 524. Adjusting the axial icon 524 may cause an axis/axes and a response range icon 526 to be displayed and placed on the user interface 116 and/or the user interface 154 on top of the still image or video 522 and the user or the wearer can adjust this into position over the still image or video 522.

FIG. 5C presents a three-dimensional view of the axial icon 524. The x plane 528, the y plane 530, and the z plane 532. They are depicted in a three-dimensional orientation. It is on these planes that graphic representations of the movement data can be displayed. The construction of these views is assembled by the KAT application software 158. Where the display of the user interface 116 and/or the display of the user interface 154 are capable of transmitting color, it is noted herein the x plane 528, the y plane 530, and the z plane 532 may be represented by the same or different colors. For example, the color may correspond to a correct movement or position being achieved. By way of another example, the color may be independent of the movement or position.

FIG. 5D shows an expanded view of only one plane (e.g., the x plane 528) of the tri-axial icon 524 with the response range icon 526 for the target data. The response range icon 526 represents the graphical overlay that the user would see displayed over the still image of video 522. The target position may be represented by element 534, and may be the position the wearer ideally wants to mimic. The target position may be bounded by a lower bound 536 and an upper bound 538. For example, the bounds 536, 538 may be equally-spaced from the element 534 where the margin of error is symmetric. By way of another example, the bounds 536, 538 may be unequally-spaced from the element 534 where the margin of error is asymmetric. The response range icon 526 may include a lower margin of error arc 540 between the element 534 and the lower bound 536, and a higher margin of error arc 542 selected on the other side of the target between the element 534 and the upper bound 538.

It is noted herein the axial icon 524 and the response range icon 526 being overlaid on the still image or video 522 may be a benefit for people who think in terms of relative distance rather than absolute numbers. By seeing the graphic overlay on the picture, the wearer and the user will be better able to understand and visualize the wearer's position and movement as it relates to the sensor data displayed on the still. It is noted herein, however, that the graphical representation is not limited to the axial icon 524 and the response range icon 526 but may instead include other representations such as, but not limited to, movement or position bars, or the like (e.g., as illustrated in FIG. 5E).

Although the above non-limiting example is directed to a still image, it is contemplated the KAT 102 and the external computing device 106 may have the processing, storage, and graphic capabilities to overlay the tri-axial icon and movement planes on a video stream.

Referring now to FIG. 5F, in another embodiment the user interface 500 may include an identifier 546 (e.g., wearer name, session name, or the like). In another embodiment, the user interface 500 may include a timer 548. For example, the timer may be a stopwatch function illustrating an elapsed local time or an indicator of elapsed global time.

In another embodiment, the user interface 500 may include a Freestyle control 550, where the user/wearer self-initiates movements at will in an unstructured manner, without any cues or commands to the wearer to indicate the beginning or end of sets, repetitions, or movements (e.g., aside from a "Delay after GO" and/or a "Pause" option). The Freestyle structure may be considered as being associated with early stages of motor learning. In the Freestyle setting, feedback is delivered per set parameters via standard methods. In addition, the wearer may broadly explore and/or experiment with the movement. Further, kinematic data may be recorded, but any "marker" to identify instances of beginning or end of movements may require manual input via gesture and/or voice activated controls, (e.g., through retrocapture processes).

In another embodiment, the user interface 500 may include a graphical user interface (GUI) window 552 including one or more steps of a cued practice session where the user/wearer initiates (starts and stops) the movements based on different audio or vibratory cues pre-set by the user and/or the wearer. The Cued Practice structure may be considered as being associated with the middle, associative stages of motor learning. The cues automatically embed "marker" in the data. When the user follows the cues during the practice, the KAT 102 may isolate and extract the data that contains only the exact movement or position desired for one or more of later review and/or analysis, for immediate performance results, and/or to store off-site (e.g., on a third-party server, on the external computing device 106, or the like).

During Cued Practice, a wearer can set and adjust audio or vibratory cues (e.g., cues distinguishable from the adjustable sounds or vibrations delivered for feedback based on kinematics) to create start-stop commands during practice. In one non-limiting example, adjustments may include, but are not limited to, a dose, type, and/or timing of number of sets; a dose, type, and/or timing of repetitions; rest periods between each repetition; what target/positions or groups of targets/positions; in what order movements or positions are formed, what duration per position; the dose, type and/or timing of feedback such as intensity, frequency, and/or loudness (e.g., including custom audio sounds player over music) based on performance (e.g., pre-set goals); or the like to achieve a completely customizable practice structure based on known pedagogical principles.

In another non-limiting example, the GUI window 552 may include, but is not limited to, a session name, a number of repetitions per set, a number of sets, an initial start time, a duration of movement or position, an interval between movements or positions, feedback type, feedback method, feedback level, recording options, or the like. It is noted herein the area with the GUI window 552 may first be occupied with a cued practice control, with which a user or a wearer initiates a Cued Practice, at which point the GUI window 552 is populated. In another embodiment, the user interface 500 may include a counter 554 indicating how far along the wearer is in the cued practice session.

Referring now to FIGS. 5E, 5F, and 6, the user interface 500 may include one or more results 556. For example, the one or more results 556 may include, but are not limited to, charts, tables, graphs, or other customized illustrations.

It is noted herein the pages of screens as illustrated in FIGS. 5A, 5B, 5E, and 5F may include, but are not limited to, actual values, zeroed-out values in relation to the captured target, a slider gauge including a range of values surrounding a target, or the like.

Referring now to FIG. 6, in another embodiment the user interface 500 may include one or more reports 558. For example, the one or more reports 558 may include, but are not limited to, an overlay of actual data and target data; an overlay of actual data, target data, and still image or video 522, charts, tables, graphs, or other customized illustrations, avatars, or other customized reports.

In one non-limiting example, a cued practice session may be performed with the system 100.

In one embodiment, the cued practice session may be performed with the system 100 by embedding-different indicators in the data being captured, measured, and logged by the system 100.

In another embodiment, the first indicator is a timestamp for each element of the data being recorded. For example, the indicator information may include various metadata indicating the user identification (ID) data, wearer ID, session information, date, time, planes activated, local and/or global margins of error, feedback settings, or the like. In another embodiment, the second indicator is a marker intentionally included in the data being recorded by the direction of the user. Using the KAT application software 158, the user may identify or mark the sequences of activity over time that the user would like to see in the practice session. For example, the user may identify when a session is to start, how many sets of repetitions of a movement or position should be performed, a duration for each repetition, any delays between the repetitions, and then when the session is to end.

In another embodiment, the KAT software application 158 logs the planned session events. The event is time-stamped and marked with a flag that includes a marker when the event occurs. For example, the timestamp (or first indicator) may be inserted at the beginning of a position or movement, and may include an audial output indicating when to start and/or when to stop moving/when to transition between positions). By way of another example, the marker (or second indicator) may be inserted at the end of a position or movement. It is noted herein the use of timestamps and/or markers enables the KAT application software 158 to very quickly search and review recorded data and focus on marked data for the user or the wearer. In addition, it is noted herein the use of timestamps and/or markers enable positions and/or movements to be retroactively captured and stored in order.

In another embodiment, the marked data of interest can then be quickly presented as tabled or graphic results to the user (e.g., as illustrated in FIG. 6, which illustrates an example portal for software on the external computing device 106 for the system 100, in accordance with one or more embodiments of the present disclosure). For example, the tabled or graphic results may include, but are not limited to, the number of repetitions completed within or outside the set parameters, the degree to which the reference data (e.g., the position) was achieved, statistics regarding the mean accuracy per set and total session in achieving the position, the direction of the error (e.g., dysmetria, the overshoot or undershoot of the performance movement relative to the position), to what degree and frequency overshoots and undershoots might be, or the like. The display screens, produced by the KAT application software 158, that present the results may be configured to convey with graphics alone, statistics alone, and/or combined graphics and statistics overlaid on a picture. In this regard, real-time or nearly real-time results (e.g., taking into consideration processing lag, in one non-limiting example) may be displayed on the user interface 154.

In one embodiment, the cued practice session may include feedback selected as cues for a session stage, a movement or position time, a movement or position set, a position or movement repetition, a position or movement performed by the wearer as defined by a particular session mode (e.g., a successful Good/In position or movement (e.g., under Instruction mode 200), a successful Good/Out position or movement, (e.g., under Exploration mode 202, a successful Bad/In position or movement (e.g., under Alert mode 204), a successful Bad/Out movement (e.g., under Comprehension mode 206), or the like), or the like. For example, the cued practice session may include one or more feedback types 216. For instance, having different feedback types 216 may allow for different practice schedules (e.g., ranging between blocked practice schedules, random-blocked practice schedules, and random practice schedules) with different positions or movements at different times during a single session. In addition, having different feedback types 216 may help schedule the timing of performance events. In addition, cues can be managed by the user or the wearer using different time points with different delays, which may change the structure of the practice session.

For example, the cues may include, but are not limited to, a Delay before the Start Cue. For instance, the cue may allow time to the user to prepare (e.g., gather equipment, set posture, or the like). By way of another example, the cues may include, but are not limited to, a Set Start Cue. For instance, the cue may signify the start of a practice. In one non-limiting example, these two cues combined may include three short feedback responses followed by a single longer feedback response.

By way of another example, the cues may include, but are not limited to, a Set End Cue. For instance, the cue may signify the end of a practice. In one non-limiting example, the cue may include three short feedback responses.

By way of another example, the cues may include, but are not limited to, the number of individual repetitions per set. For instance, the cue may indicate how many times a motion will be practiced. In one non-limiting example, the cue may include an audio speech recording of the specific number.

By way of another example, the cues may include, but are not limited to, the Repetitions Delay. For example, the cue may be the delay time between when individual repetitions start. In one non-limiting example, the cue may be a fixed or constant delay. In another non-limiting example, the cue may be a periodic, variable delay. It is noted herein a variable repetition delay rate may be set by the user or the wearer before a practice session. Here, the user or the wearer may first press a Set Structure triggering key on the KAT 102. Then the wearer performs the repetitive movement at a specific pace, and the KAT 102 will measure and learn the Cues and timing delays from the setting session, which may be stored on a per-athlete basis and/or a per-movement basis.

By way of another example, the cues may include, but are not limited to, a Duration of movement. For example, the cue may be the expected time in duration that the movement is allowed and/or expected.

In one non-limiting example, data from a past performance may be captured by the system 100. In one embodiment, a wearer may experience one trial in a practice session that the user or the wearer believes was successful. The user or the wearer could then define a new set of reference data using the recorded training data of the successful trial for one or more movement planes, as the user or the wearer observes the last repetition was a superior example. For example, a wearer may decide a golf swing repetition was successful, and may activate a retroactive capture of the past performance to catch hip-shoulder timing, delay (lag), post-swing movement kinematics, angular acceleration, eye movement, gaze duration, or the like. The wearer would then enter a triggering signal on the KAT 102 (e.g., a double tap or triple tap on the one or more user input devices 118), and the data associated with the last repetition would then be recorded for the user or the wearer as a reference trial and/or a marked trial for future display analysis (e.g., on the KAT 102 and/or on the external computing device 106), during which salient kinematic components of successful positions or movements may be extracted and compared.

The cued practice session may allow a user to set the practice schedule. For example, if a user is learning at 3 different movements or positions, the user can choose the order and duration to practice them. The KAT 102 will give cues of which 'position' to do, and for how long, providing a custom cued practice schedule feature based on either a "blocked practice" schedule, a "random-blocked practice", or a "random practice" schedule, as described throughout the present disclosure.

It is noted herein the embodiments and/or examples previously discussed herein may be usable with both Cued Practice and with Freestyle practice, for purposes of the present disclosure.

FIGS. 7A-7F illustrate a method or process 700 for providing kinesthetic awareness, in accordance with one or more embodiments of the present disclosure. It is noted herein that the steps of method or process 700 may be implemented all or in part by the system 100. It is further recognized, however, that the method or process 700 is not limited to the system 100 in that additional or alternative system-level embodiments may carry out all or part of the steps of method or process 700.

In a step 702, one or more KATs are obtained. In one embodiment, the KAT 102 is as described throughout the present disclosure. For example, the KAT 102 may include the controller 108, the one or more sensors 120, and the one or more feedback devices 122. In another embodiment, desired movements and/or positions (targets) are set by the primary wearer or a user (e.g., coach, clinician, therapist or other expert) who has knowledge about the desired movement and/or positions. In another embodiment, the KAT 102 is coupled to or held by the wearer. To begin a training session, the wearer first positions the KAT 102 about the desired body part to monitor. It is noted herein the KAT 102 may have already been in possession of a wearer, such that step 702 may be considered optional.

In a step 704, a set of reference data is captured with the one or more sensors. In one embodiment, the KAT 102 has three modes of operation, including a "Capture" mode, a "Run" mode, and a "Reference" mode. For example, in a Capture mode the KAT 102 collects data, using the one or more sensors 120. For instance, the data may include a set of reference data which is used in the Run mode to calculate a numerical response. In another embodiment, the set of reference data is stored in memory. For example, the user may modify the set of reference data in the Reference mode. The KAT 102 organizes the set of reference data into one or more positions defined as allowable ranges (minimum and maximum) of values of the parameters of the one or more sensors 120.

It is noted herein some combination of the functions of the Reference mode and/or the Capture mode may be displayed and/or controllable via a Capture or Set Up Screen of the KAT application software 158. In addition, it is noted herein some combination of the functions of the Run mode may be displayed and/or controllable via a Cued Practice Screen of the KAT application software 158. Further, it is noted herein results may be displayed via a Results Screen of the KAT application software 158. It is noted herein the user interface 500 may be configured with different sets of software and/or physical hardware, where the sets of software and/or physical hardware are selected based on a model type of the KAT 102 (and the system 100, where the system 100 is self-contained), type of subscription service, or the like. For example, the KAT 102 and/or other components of the system 100 may include basic or advanced displays, app screens, or the like based on a model type of the KAT 102 (and the system 100, where the system 100 is self-contained), type of subscription service, or the like.

In another embodiment, the Capture mode may be initiated once the KAT 102 is secured to the wearer/tool. For example, the Capture mode may be initiated either through the one or more user input devices 118 or the software application (e.g., on the one or more external computing devices 106). The goal of the Capture mode is to allow the user to automatically capture the set of reference data which will be used to define the one or more positions. To collect the set of reference data, the user starts a Capture Session. For example, the Capture Session may be either static or dynamic.

In another embodiment, a Static Capture Session includes a temporal component at which or during which a relative timing of positions is captured. The Static Capture Session includes recording the one or more positions with a configurable transition interval between each of the positions, where the number of positions is defined by the user. The transition interval may be 1.5 or three seconds by default;

however, the user can adjust the value of the transition interval through the one or more user input devices 118 or the software application (e.g., on the one or more external computing devices 106). Each of the positions is maintained for a recording duration, during which the one or more sensors 120 continuously collect data. The recording duration for each of the positions is set to five seconds by default but may be configured through the one or more user input devices 118 or the software application as well. The KAT 102 is supposed to be held still at each of the positions while collecting the set of reference data but has to be moved to the subsequent position within the transition interval.

In another embodiment, more than one position may be recorded during the Static Capture Session. For example, the set of reference data may include a data sub-set for each of the positions. The data sub-set for each of the positions is captured for the length of the recording duration and statistics such as minimum and maximum value, median, mean, and standard deviation are calculated. A configurable sampling rate (usually between 10-100 samples per second) may be adjusted by the user and is used to determine the amount of data collected during the recording duration for each of the positions. When recording multiple positions, the user starts at an initial position, at which the one or more sensors 120 gather the data sub-set for the initial position. After recording the data sub-set for the initial position, the user transitions to a subsequent position within the transition interval. The one or more sensors 120 then gather the data sub-set for the subsequent position. This process is continued until the data sub-set has been collected for a final position in the sequence. Once the data sub-set for each of the positions has been captured, the set of reference data is stored in memory by the controller 108 and/or the controller 146. The controller 108 and/or the controller 146 defines the allowable range of parameters gathered by the one or more sensors 120 for each of the positions using a median filter and empirically predetermined standard errors and statistics measured during the capture session.

By way of another example, the set of reference data may include a timestamp for each of the one or more positions. For instance, the time stamp may be based on a global timestamp, including a time and date for each position while the Capture mode is run. In addition, the time stamp may be a localized time stamp, representing a time-elapsed amount for each position while the Capture mode is run. The timestamp may reflect the recording duration for each of the positions and/or the transition interval between each of the positions.

In another embodiment, a Dynamic Capture Session includes the user specifying the duration of the overall capture session and the number of positions that should be defined based on the set of reference data captured during the Static Capture Session. The controller 108 and/or the controller 146 determine the boundaries of each of the positions automatically and define the allowable ranges for each of the positions based on the medians and standard deviations of each parameter recorded by the one or more sensors 120. In its behavior, Dynamic Capture is similar to the multi-point scenario of Static Capture but instead of holding the KAT 102 still for the length of the recording duration and moving the KAT 102 only during the transition interval, the user moves the KAT 102 freely, performing all movements. The KAT 102 then decides on how to organize and cluster the set of reference data into the data sub-set for each of the positions. It is noted herein the set of reference data may include timestamps for each of the positions.

In another embodiment, the Dynamic Capture Session may collect a few seconds of continuous data for a position or movement (e.g., a full tennis swing including, but not limited to, preparation of stance, swing, contact, and follow-through). For example, the data may be collected as a continuous waveform. The Dynamic Capture Session may compare actual data with target data using regular references at regular time intervals, (e.g., to be a co-registration of gait cycle, swing path, or the like), at a pre-determined event (e.g., at a specific shin height, peak hip rotational acceleration, or the like) or use specific kinematics (e.g., to determine a beginning and end of gait cycle, swing path, or the like). For example, the Dynamic Capture Session may be beneficial to train a wearer for prosthetic use.

In another embodiment, the set of reference data may be generated via artificial intelligence (AI) and/or enhanced analytic capabilities of the system 100 and/or components of the system 100. For example, machine learning, deep learning, 3D and/or 6D computational vision, and/or pose estimation methods, may be utilized to exact three-dimensional static and dynamic data from two-dimensional images or video. In this regard, the enhanced analytic methods may be utilized to predict and track object/person kinematic patterns over time for use in optimal feedback delivery based on prior performance.

Figure 7A:
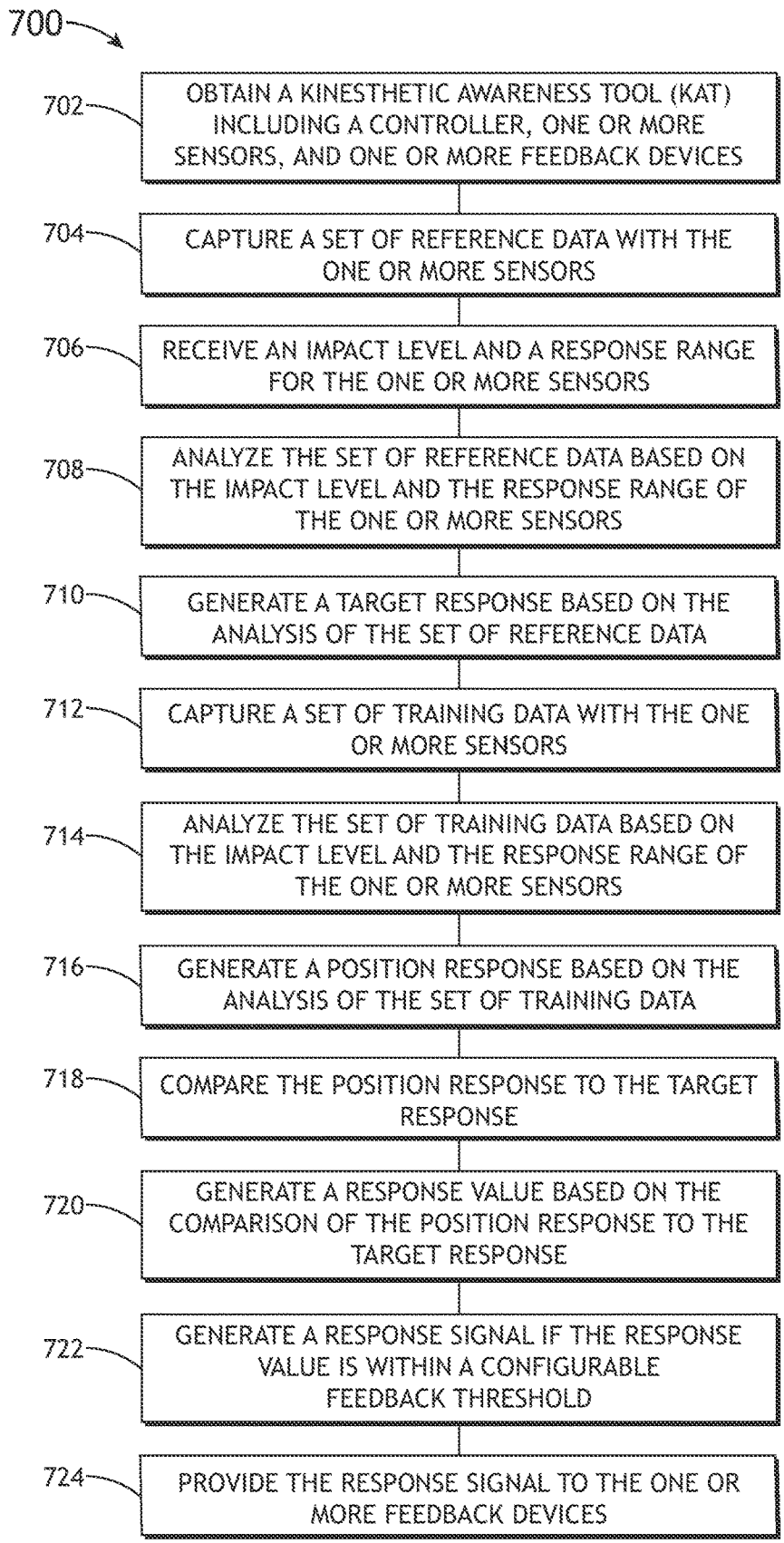
FIG. 7A is a flow diagram illustrating a method or process for providing kinesthetic awareness, in accordance with one or more embodiments of the present disclosure.
Figure 7B:
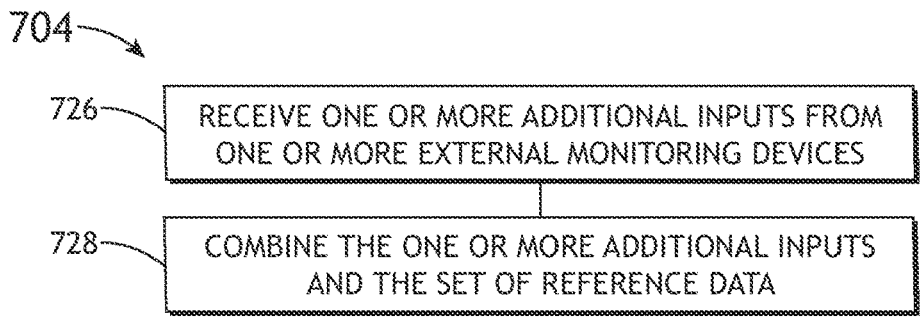
FIG. 7B is a flow diagram illustrating a method or process for providing kinesthetic awareness, in accordance with one or more embodiments of the present disclosure.

Referring now to FIG. 7B, in a step 726 one or more additional inputs may be received from one or more external monitoring devices. In a step 728, the one or more additional inputs and the set of reference data are combined. For example, combining may refer to adding (e.g., leading, inserting, appending, or the like) the one or more additional inputs to the set of reference data. By way of another example, combining may refer to replacing at least a portion of the set of reference data with the one or more additional inputs.

The receiving and/or combining may occur at any point or number of points during the Static Capture session and/or the Dynamic Capture session. For example, the controller 108 and/or the controller 146 may receive an additional sensor input from the external monitoring device 104 during the Capture mode. When implementing the Capture mode, the controller 108 and/or the controller 146 combines the additional sensor input into the set of reference data. As such, the additional sensor input is used when the target response is generated.

It is noted herein the additional sensor input may be generated by a different wearer, and may be used as a baseline or reference set for the wearer whose movements or positions are being evaluated. In this regard, step 704 may be performed with a KAT 102 separate from the KAT 102 worn by the wearer whose movements or positions are being evaluated.

It is noted herein the set of reference data may be captured in real-time, or may be captured through retroactive capturing procedures as described throughout the present disclosure.

Figure 7C:
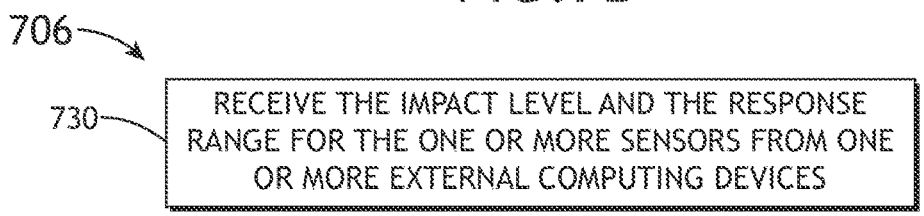
FIG. 7C is a flow diagram illustrating a method or process for providing kinesthetic awareness, in accordance with one or more embodiments of the present disclosure.

Referring again to FIG. 7A, in a step 706 an impact level and a response range is received for the one or more sensors. In one embodiment, once the set of reference data has been collected, the user or the wearer can initiate the Reference mode. In another embodiment, the Reference mode allows the user and/or the wearer to review and edit each of the positions. The user and/or the wearer may edit an impact level and a response range for each of the one or more sensors 120. The user or the wearer may edit the response range (e.g., value boundaries) of each parameter gathered by the one or more sensors 120 for each of the positions. For example, to edit the response range for a parameter, the user and/or the wearer selects the position and the parameter using the one or more user input devices 118 or the software application (e.g., on the one or more external computing devices 106). For instance, as illustrated in FIG. 7C, in a step 730, the controller 108 may receive the impact level and response range for each of the one or more sensors 120 from the external computing device 106. The user or the wearer may specify whether the minimum (e.g., the lower bound) or the maximum (e.g., the upper bound) of the response range is being changed. In the Reference mode, each of the one or more sensors 120 is sampled to provide a current value of each parameter that is monitored. The current value of each parameter may be presented in two ways. For example, the value of each parameter may be displayed to the user or the wearer through a user interface 116 of the KAT 102. By way of another example, the value of each parameter may be displayed to the user or the wearer through the external computing device 106. The user may change the bound value of the response range by confirming the currently sampled value through one of the one or more user input devices 118 or the software application (e.g., on the one or more external computing devices 106).

In another embodiment, the user may also adjust the impact level of each parameter gathered by the one or more sensors 120 for each of the positions, in addition to editing the response range of each of the one or more sensors 120. The impact level determines if and how each parameter gathered by the one or more sensors 120 has an effect on the numerical response. The impact level may be set as one of three settings: "no impact", "active impact", and "passive impact". For example, when "no impact" is selected, the selected parameter is taken into account when calculating the numerical response, as the data still records the selected parameter such that it exists in data (e.g., with timestamps and/or markers), but no feedback is delivered to a wearer that takes into account the selected parameter. By way of another example, "active impact" is used, the selected parameter impacts the numerical response when currently sampled values for the parameter are within the response range for the selected position (between the minimum value and the maximum value for the given selected parameter at the selected position). By way of another example, when "passive impact" is used, the selected parameter impacts the numerical response when currently sampled values for the parameter are outside of the response range for the selected position (lower than minimum value or higher than the maximum value).

Figure 7D:
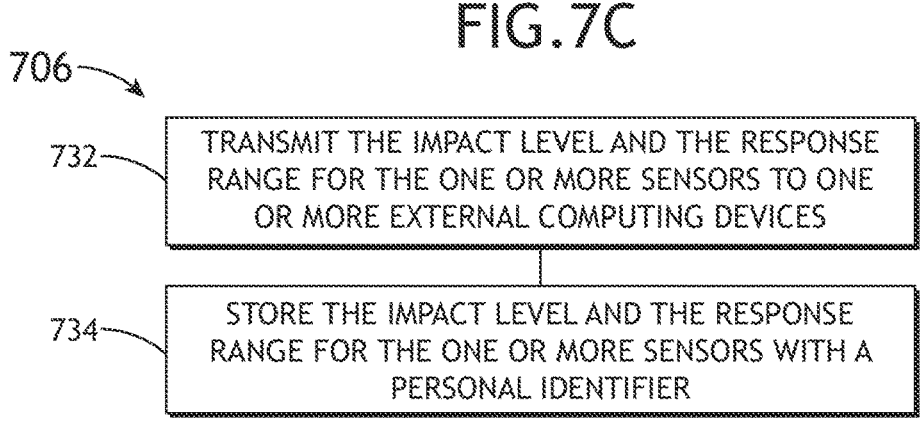
FIG. 7D is a flow diagram illustrating a method or process for providing kinesthetic awareness, in accordance with one or more embodiments of the present disclosure.

Referring now to FIG. 7D, in a step 732 the impact level and the response range for the one or more sensors is transmitted to one or more external computing devices. In one embodiment, the controller 108 may store the impact level and the response range for each of the one or more sensors 120 locally or send the impact level and the response range for each of the one or more sensors 120 to the external computing device 106, where the impact level and the response range for the one or more sensors 120, generated by the KAT 102 or received by the KAT 102 from a third-party device, is transmitted to one or more external computing devices 106.

In a step 734, the impact level and the response range for the one or more sensors is stored with a personal identifier. In one embodiment, in an effort to save the user time when repeating a training session, the external computing device 106 may include a user identification (ID) setting control. The user ID setting control may allow the user to store the impact level and the response range for each of the one or more sensors 120 in association with a unique personal identifier. For example, the personal identifier may be an alphanumeric character or string of alphanumeric characters corresponding to a particular wearer, activity, movement, time and/or date, or the like. The impact level and the response range for each of the one or more sensors 120 are stored in association with the unique personal identifier on either the controller 108 or the external computing device 106. The next time the user wishes to perform a training session, the Capture mode and Reference mode sequences may be skipped, and the user or the wearer may instead load the stored data. It is noted herein the use of the user ID setting control allows the KAT 102 to be used with multiple people, as each individual can create a unique profile with which to associate data.

Referring again to FIG. 7A, in a step 708 the set of reference data is analyzed based on the impact level and the response range of the one or more sensors. In one embodiment, the response range and the impact level for each parameter at each of the positions is stored in memory by the controller 108 and/or the controller 146. The controller 108 and/or the controller 146 then analyzes the set of reference data according to the impact level and the response range set for each of the one or more sensors 120 at each of the positions.

In a step 710, a target response is generated based on the analysis of the set of reference data. In one embodiment, based on the analysis in step 708, the controller 108 and/or the controller 146 generates a target response. For example, the target response may be a singular value or sub-division of numbers. For instance, a target value may be provided for each parameter of each of the positions. The target response provides the data set to which all subsequent data is compared during the Run mode in order to provide the user with feedback in regards to achieving each of the positions with the desired degree of accuracy.

Although embodiments of the disclosure illustrate the capturing of a set of reference data of step 704, receiving an impact level and a response range of step 706, analyzing the set of reference data based on the impact level and the response range of step 708, and generating a target response based on the analysis of the set of reference data, in some embodiment, at least one of the set of reference data, the impact level, the response range, and/or the target response may be pre-loaded into the KAT 102. In these embodiments, one or more of steps 704, 706, 708, and/or 710 may be optional.

In a step 712, a set of training data is captured with the one or more sensors. In one embodiment, the Run mode is used to provide the user or the wearer with real-time feedback by comparing currently sampled data to the target response and actuating one or more of the feedback devices accordingly. In the Run mode, the KAT 102 may continuously (e.g., in real time) capture a training set of data from the one or more sensors 120 for each repetition through the one or more positions. It is noted herein the training data may be visually overlaid with the reference data.

Figure 7E:
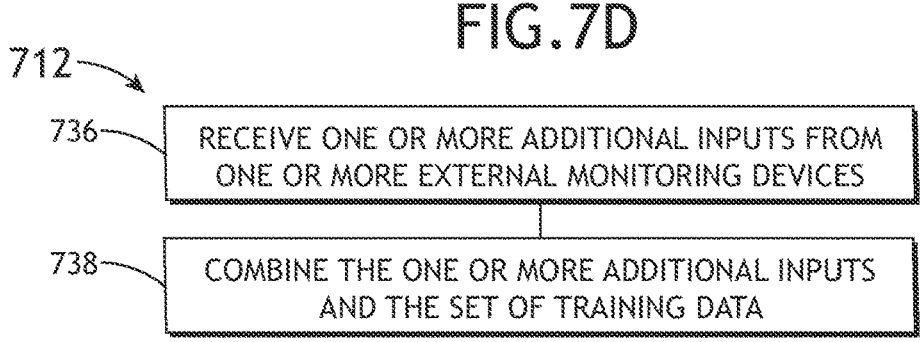
FIG. 7E is a flow diagram illustrating a method or process for providing kinesthetic awareness, in accordance with one or more embodiments of the present disclosure.

Referring now to FIG. 7E, in a step 736 one or more additional inputs are received from one or more external monitoring devices. In a step 738, the one or more additional inputs and the set of training data are combined. For example, combining may refer to adding (e.g., leading, inserting, appending, or the like) the one or more additional inputs to the set of training data. By way of another example, combining may refer to replacing at least a portion of the set of training data with the one or more additional inputs.

The controller 108 and/or the controller 146 may receive an additional sensor input from the external monitoring device 104 during the Run mode. When the Run mode is implemented, the controller 108 and/or the controller 146 may combine the additional sensor input sampled into the set of training data. As such, the additional sensor input sampled is used when the current response (e.g., position response) is generated, and in turn used when a numerical response (e.g., a response value) for determining the response signal is generated.

Figure 7F:
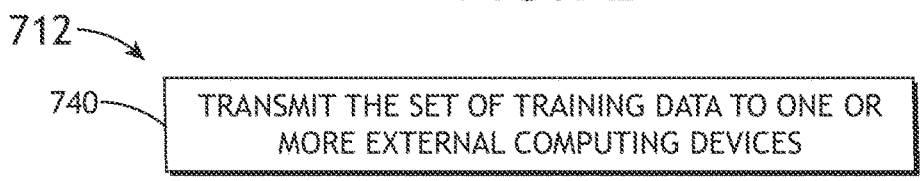
FIG. 7F is a flow diagram illustrating a method or process for providing kinesthetic awareness, in accordance with one or more embodiments of the present disclosure.

Referring now to FIG. 7F, in a step 740 the set of training data is transmitted to one or more external computer devices. In one embodiment, the system 100 may implement a practice feature, where the set of training data for each repetition and the number of correct and/or incorrect repetitions is collected and stored for each practice session, to allow the user or the wearer to track progress over multiple training sessions. For example, before each practice session, the user or the wearer can set performance goals to reach during the current practice session. For instance, feedback may be activated to let the user or the wearer know when the desired number of corrected movements has been completed. In addition, the number of correct repetitions completed within a set time span may be counted. The data may be stored for each user in the memory 114, and/or transmitted via various wireless methods, as mentioned above. The set of training data for each repetition may be stored in association with the unique personal identifier to allow the user to access and track the data. The set of training data for each repetition may be stored locally by the controller 108. In the alternative, the controller 108 may send the set of training data for each repetition to the external computing device 106, and the set of training data for each repetition may be stored in the memory 152.

It is noted herein the steps 704 and/or 712 of the method or process 700 may be programmed for sequential movements (e.g., during Dynamic Capture) captured via multiple sensors 120 and/or external monitoring devices 104 to track a complex sequence of movement. For example, sensor one must determine that a certain parameter is met before sensor two detects its own pre-set distance and before the feedback is delivered.

Referring again to FIG. 7A, in a step 714 the set of training data is analyzed based on the impact level and the response range of the one or more sensors to determine a position response. In one embodiment, the controller 108 and/or the controller 146 may then calculate the current response (e.g., position response) for the set of training data, which indicates how well the currently sampled data from the one or more sensors 120 corresponds to the reference data stored for each of the positions. For example, the current response (e.g., position response) may be based on the impact level and response range for each of the one or more sensors 120. To generate the current response (e.g., position response), the controller 108 and/or the controller 146 may analyze the set of training data according to the impact level and the response range of each of the one or more sensors 120. For example, the current response (e.g., position response) may be a singular value or sub-division of numbers. For instance, a current value may be provided for each parameter of each of the positions.

In a step 718, the position response is compared to the target response. In one embodiment, the controller 108 and/or the controller 146 may compare the current response (e.g., the position response) to the target response.

In a step 720, a response value is generated based on the comparison of the position response. In one embodiment, a numerical response (or response value) is generated based on the comparison in step 718. The numerical response may be calculated as the maximum of the current value for each of the positions. For example, the current value for each of the positions is calculated by checking if sampled data is within the response range for any of the parameters set on "active impact". By way of another example, the current value for each of the positions is calculated by checking if sampled data is outside the response range for any of the parameters set on "passive impact". The checking may be done for each of the one or more positions and every parameter. Once calculated, the current value for each of the positions is summed and normalized by the number of parameters of which the impact is different than none to generate a normalized current value for each of the positions. This allows for comparison between each of the positions. After normalization, the maximum value and its index is extracted from the normalized current values and stored as the numerical response to determine which of the one or more positions is the most likely for the KAT 102 to be at and what is the measure of the fit.

The numerical response may be provided as a numerical value between 0-100%. For example, 0% means that none of the set of training data corresponds to any of the set of reference data. By way of another example, 100% indicates that the set of training data is within the response range of all "active impact" parameters and outside of the response range of all "passive impact" parameters of at least one of the positions. It corresponds to how "far away" the set of training data is from the set of reference data. This strategy may be described as the "winner takes all" among each of the one or more positions.

In a step 722, a response signal is generated if the response value is within a configurable feedback threshold. In one embodiment, the KAT 102 allows for the user to set the configurable feedback threshold. For example, the configurable feedback threshold may be set anywhere between 0-100%. In another embodiment, feedback may be configured to be either active or passive. For example, in active feedback mode the feedback strength is proportional to the numerical response when the numerical response is above the configurable feedback threshold and approaching (or set) to 0% when below. For instance, active feedback mode may serve as a positive detector. By way of another example, in passive feedback mode the feedback strength is approaching (or set to) 100% when the numerical response is below the configurable feedback threshold and approaching 0% (or set to) when the numerical response is above the configurable feedback threshold. It is noted herein the feedback strength may be used as a type of feedback level 220 to modulate the type of selected feedback type 216 (e.g., acoustic, visual, haptic, kinetic, or the like). The configurable feedback threshold may be based on the "Instruction" mode 200, the "Exploration" mode 202, the "Alert" mode 204, or the "Comprehension" mode 206, as previously described herein.

In a step 724, the response signal is provided via the one or more feedback devices. In another embodiment, if the numerical response is within the configurable feedback threshold, then the one or more feedback devices 122 provides a response signal to inform the wearer. The response signal from the one or more feedback devices 122 may be generated as one or more feedback types 216, in one or more feedback methods 218, and/or at one or more feedback levels 220. In one embodiment, the response signal is provided to the wearer via the one or more feedback devices 122.

It is noted herein the method or process 700 is not limited to the steps and/or sub-steps provided. The method or process 700 may include more or fewer steps and/or sub-steps. The method or process 700 may perform the steps and/or sub-steps simultaneously. The method or process 700 may perform the steps and/or sub-steps sequentially, including in the order provided or an order other than provided. Therefore, the above description should not be interpreted as a limitation on the scope of the present disclosure but merely an illustration.

It is further contemplated that each of the embodiments of the method or process 700 described above may include any other step(s) of any other method(s) described herein. In addition, each of the embodiments of the method or process 700 described above may be performed by any of the systems described herein.

As such, advantages of the present disclosure are directed to a system and method for providing kinesthetic awareness. Advantages of the present disclosure also include a kinesthetic awareness tool (KAT) to be used for training feedback, which is managed by a controller monitoring one or more sensors capture training and performance data, analyzing that data, and controlling one or more feedback devices.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software may become significant) a design choice representing cost vs. efficiency tradeoffs. Those having skill in the art will appreciate that there are various vehicles by which processes and/or systems and/or other technologies described herein may be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be affected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media holds or transmits device-detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled, implemented, translated, and/or converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein may be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory systems, automation security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which may be implemented, individually and/or collectively, by a wide range of hardware, software, firmware, and/or any combination thereof may be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein may be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although a user is shown/described herein as a single illustrated figure, those skilled in the art will appreciate that the user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mate-able and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B".

With respect to the claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although the invention has been explained in relation to its preferred embodiment, it is to be understood that many other possible modifications and variations may be made without departing from the spirit and scope of the invention as hereinafter claimed.

What is claimed:

1. A system for providing kinesthetic awareness comprising:
   a kinesthetic awareness tool for providing kinesthetic awareness, comprising:
      a controller, wherein the controller is communicatively coupled to a plurality of sensors selectively placed on one of a body part or a tool based on one of a desired movement or a desired position, wherein the controller includes one or more processors, wherein the one or more processors are communicatively coupled to memory, wherein the one or more processors are configured to execute a set of program instructions maintained in the memory and configured to cause the one or more processors to:
         capture a set of reference data with the plurality of sensors, wherein the captured set of reference data includes one of the desired movement or the desired position set by one of a user or a wearer, wherein one of the user or the wearer holds knowledge about one of the desired movement or the desired position;
         capture a set of training data with the plurality of sensors based on one of the desired movement or the desired position set by one of the user or the wearer;
         analyze the set of training data based on an impact level for each sensor of the plurality of sensors and a response range for each sensor of the plurality of sensors, wherein the impact level for each sensor of the plurality of sensors and the response range for each sensor of the plurality of sensors is received from one of the user or the wearer;

generate a position response for the set of training data based on the analysis of the set of training data;

compare the position response to a target response, wherein the target response is generated based on an analysis of a set of reference data; and generate a response value based on a comparison of the position response to the target response.

2. The system of claim 1, wherein the one or more processors are configured to execute the set of program instructions maintained in the memory and configured to cause the one or more processors to:

receive the impact level and the response range for the plurality of sensors;

analyze the set of reference data based on the impact level and the response range of the plurality of sensors; and generate the target response based on the analysis of the set of reference data.

3. The system of claim 2, wherein the kinesthetic awareness tool includes a triggering key, wherein at least one of the set of training data or the set of reference data is captured by pressing a triggering key a first time to activate a capture window and a second time to de-active the capture window.

4. The system of claim 2, wherein the kinesthetic awareness tool includes a triggering key, wherein at least one of the set of training data or the set of reference data is captured by pressing a triggering key a first time to activate a timed capture window.

5. The system of claim 2, further comprising:
one or more external monitoring devices.

6. The system of claim 5, wherein at least one of the impact level of the plurality of sensors, the response range of the plurality of sensors, or the target response are received from the one or more external monitoring devices.

7. The system of claim 5, wherein the one or more processors are configured to execute a set of program instructions maintained in the memory and configured to cause the one or more processors to:

receive one or more additional inputs from the one or more external monitoring devices; and combine the one or more additional inputs and the set of reference data.

8. The system of claim 5, wherein the one or more processors are configured to execute a set of program instructions maintained in the memory and configured to cause the one or more processors to:

receive one or more additional inputs from the one or more external monitoring devices; and combine the one or more additional inputs and the set of training data.

9. The system of claim 5, wherein the set of training data includes a plurality of measurements for a plurality of positions performed in at least one plane.

10. The system of claim 9, wherein the set of training data includes a timestamp for at least one measurement of the plurality of measurements corresponding to at least one position of the plurality of positions.

11. The system of claim 9, wherein the set of training data includes a timestamp or marker for at least one measurement of the plurality of measurements corresponding to at least one movement of a plurality of movements.

12. The system of claim 9, the kinesthetic awareness tool further comprising:
a plurality of feedback devices, wherein the one or more processors are configured to execute a set of program instructions maintained in the memory and configured to cause the one or more processors to:

generate a response signal if the response value is within a configurable feedback threshold; and output the response signal via the plurality of feedback devices.

13. The system of claim 12, wherein the response signal is provided via a gesture on or proximate to the kinesthetic awareness tool when the plurality of feedback devices is configured to output on-request feedback.

14. The system of claim 12, wherein the configured feedback threshold includes a range of values representing a margin of error surrounding the target response.

15. The system of claim 14, wherein the range of values corresponds to a desired position, wherein the response signal is generated when a position of the plurality of positions is within the range of values corresponding to the desired position.

16. The system of claim 14, wherein the range of values corresponds to a desired position, wherein the response signal is generated until a position of the plurality of positions is within the range of values corresponding to the desired position.

17. The system of claim 14, wherein the range of values corresponds to an undesired position, wherein the response signal is generated when a position of the plurality of positions is within the range of values corresponding to the undesired position.

18. The system of claim 14, wherein the range of values corresponds to an undesired position, wherein the response signal is generated until a position of the plurality of positions is within the range of values corresponding to the undesired position.

19. The system of claim 14, wherein the range of values is symmetrically distributed on either side of the target response.

20. The system of claim 14, wherein the range of values is asymmetrically distributed on either side of the target response, where an asymmetric distribution weights a particular set of values within the range of values.

21. The system of claim 14, wherein the values are adjustable within the range via one or more sliders on a user interface.

22. The system of claim 21, wherein the one or more sliders includes a global slider, wherein the values are adjustable within the range via the global slider on the user interface.

23. The system of claim 21, wherein the one or more sliders includes a plurality of sliders, wherein the values are adjustable within the range via the plurality of sliders on the user interface.

24. The system of claim 21, wherein the user interface is configured to display at least one of a still image or a video stream.

25. The system of claim 24, wherein the user interface is configured to display an axial icon overlaid on the at least one of a still image or a video stream, wherein the axial icon includes a representation of the at least one plane in which the plurality of positions is performed.

26. The system of claim 25, wherein the user interface is configured to display a response range overlaid on the at least one of the still image or the video stream, wherein the response range includes the target response, a lower bound, a lower margin of error arc between the lower bound and the target response, a higher bound, and a higher margin of error arc between the higher bound and the target response.

27. The system of claim 21, the kinesthetic awareness tool further comprising the user interface.

28. The system of claim 21, further comprising:
an external computing device.

29. The system of claim 28, wherein the external computing device and the kinesthetic awareness tool are configured to be communicatively coupled directly through respective communication interfaces.

30. The system of claim 28, wherein the external computing device and the kinesthetic awareness tool are configured to be communicatively coupled indirectly through a server via respective communication interfaces.

31. The system of claim 30, wherein the external computing device is configured to control the kinesthetic awareness tool via the server.

32. The system of claim 21, wherein the one or more processors are configured to execute a set of program instructions maintained in the memory and configured to cause the one or more processors to:
generate a response signal based on one or more cues during a Cued Practice session for at least one of a position time, a position set, a position repetition, or a position performed by the wearer as defined by a particular session mode.

33. A method for providing kinesthetic awareness comprising:
capturing a set of reference data with a plurality of sensors, wherein the plurality of sensors are selectively placed on one of a body part or a tool based on one of a desired movement or a desired position, wherein the captured set of reference data includes one of the desired movement or the desired position set by one of a user or a wearer, wherein one of the user or the wearer holds knowledge about one of the desired movement or the desired position;
capturing a set of training data with the plurality of sensors of a kinesthetic awareness tool based on one of the desired movement or the desired position set by one of the user or the wearer;
analyzing the set of training data based on an impact level for each sensor of the plurality of sensors and a response range for each sensor of the plurality of sensors, wherein the impact level for each sensor of the plurality of sensors and the response range for each sensor of the plurality of sensors is received from one of the user or the wearer;
generating a position response for the set of training data based on the analysis of the set of training data;
comparing the position response to a target response, wherein the target response is generated based on an analysis of a set of reference data; and
generating response value based on a comparison of the position response to the target response.

34. The method of claim 33, further comprising:
receiving the impact level and the response range for the plurality of sensors;
analyzing the set of reference data based on the impact level and the response range of the plurality of sensors; and
generating the target response based on the analysis of the set of reference data.

35. The method of claim 33, further comprising:
generating a response signal if the response value is within a configurable feedback threshold; and
outputting the response signal via a plurality of feedback devices.

36. A kinesthetic awareness tool for providing kinesthetic awareness comprising:
a controller, wherein the controller is communicatively coupled to a plurality of sensors selectively placed on one of a body part or a tool based on one of a desired movement or a desired position, wherein the controller includes one or more processors, wherein the one or more processors are communicatively coupled to memory, wherein the one or more processors are configured to execute a set of program instructions maintained in the memory and configured to cause the one or more processors to:
capture a set of reference data with the plurality of sensors, wherein the captured set of reference data includes one of the desired movement or the desired position set by one of a user or a wearer, wherein one of the user or the wearer holds knowledge about one of the desired movement or the desired position;
capture a set of training data with the plurality of sensors based on one of the desired movement or the desired position set by one of the user or the wearer;
analyze the set of training data based on an impact level for each sensor of the plurality of sensors and a response range for each sensor of the plurality of sensors, wherein the impact level for each sensor of the plurality of sensors and the response range for each sensor of the plurality of sensors is received from one of the user or the wearer;
generate a position response for the set of training data based on the analysis of the set of training data;
compare the position response to a target response, wherein the target response is generated based on an analysis of a set of reference data; and
generate response value based on a comparison of the position response to the target response.

37. The tool of claim 36, wherein the one or more processors are configured to execute the set of program instructions maintained in the memory and configured to cause the one or more processors to:
receive the impact level and the response range for the plurality of sensors;
analyze the set of reference data based on the impact level and the response range of the plurality of sensors; and
generate the target response based on the analysis of the set of reference data.

38. The tool of claim 36, further comprising:
a plurality of feedback devices,
wherein the one or more processors are configured to execute a set of program instructions maintained in the memory and configured to cause the one or more processors to:
generate a response signal if the response value is within a configurable feedback threshold; and
output the response signal via the plurality of feedback devices.

* * * * *